(12) United States Patent
Imamura

(10) Patent No.: US 10,791,920 B2
(45) Date of Patent: Oct. 6, 2020

(54) IMAGE FORMING APPARATUS AND IMAGE FORMING METHOD

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 605 days.

(21) Appl. No.: 14/366,357

(22) PCT Filed: Feb. 13, 2013

(86) PCT No.: PCT/JP2013/054066
§ 371 (c)(1),
(2) Date: Jun. 18, 2014

(87) PCT Pub. No.: WO2013/125547
PCT Pub. Date: Aug. 29, 2013

(65) Prior Publication Data
US 2014/0333749 A1 Nov. 13, 2014

(30) Foreign Application Priority Data

Feb. 20, 2012 (JP) ................. 2012-034538

(51) Int. Cl.
*A61B 3/00* (2006.01)
*A61B 3/12* (2006.01)
(Continued)

(52) U.S. Cl.
CPC .......... *A61B 3/0025* (2013.01); *A61B 3/1233* (2013.01); *A61B 5/02416* (2013.01);
(Continued)

(58) Field of Classification Search
CPC ........... H04N 5/23212; H04N 5/23219; H04N 5/23248; G06T 2207/10016;
(Continued)

(56) References Cited

U.S. PATENT DOCUMENTS 7,549,746 B2 6/2009 Tsukada et al.
8,355,622 B2 1/2013 Harada
(Continued)

FOREIGN PATENT DOCUMENTS

CN 101043841 A 9/2007
CN 101483783 A 7/2009
(Continued)

OTHER PUBLICATIONS

Mar. 19, 2013 International Search Report and Written Opinion in International Patent Appln. No. PCT/JP2013/054066.
(Continued)

*Primary Examiner* — Farhan Mahmud
(74) *Attorney, Agent, or Firm* — Venable LLP

(57) ABSTRACT

An image forming apparatus determines an exceptional frame of a plurality of frames of a moving image of an eye based on the image features of each frame, and changes a moving image forming method based on the determined exceptional frame. For example, the image forming apparatus generates a new moving image by extracting a frame sequence including frames extracted from the moving image not to include a frame which has been determined as an exceptional frame.

18 Claims, 17 Drawing Sheets

(51) Int. Cl.
    *A61B 5/024*     (2006.01)
    *G06T 3/40*     (2006.01)
    *G06T 7/00*     (2017.01)
    *A61B 3/10*     (2006.01)

(52) U.S. Cl.
    CPC .......... *G06T 3/4038* (2013.01); *G06T 7/0016* (2013.01); *A61B 3/1015* (2013.01); *G06T 2207/10016* (2013.01); *G06T 2207/30041* (2013.01); *G06T 2207/30101* (2013.01)

(58) Field of Classification Search
    CPC . G06T 2207/30041; G06T 2207/10101; G06T 7/0012; G01B 9/02091; A61B 3/145; A61B 3/102; A61B 3/12; A61B 3/14; A61B 3/152
    See application file for complete search history.

(56) References Cited

U.S. PATENT DOCUMENTS

| | | | |
|---|---|---|---|
| 8,705,826 B2 | 4/2014 | Liu et al. | |
| 2002/0047936 A1* | 4/2002 | Tojo | G06K 9/00711 348/700 |
| 2006/0228011 A1* | 10/2006 | Everett | A61B 3/113 382/128 |
| 2007/0067723 A1 | 3/2007 | Hosoda et al. | |
| 2007/0191677 A1 | 8/2007 | Nishimura et al. | |
| 2007/0222945 A1 | 9/2007 | Tsukada et al. | |
| 2008/0262354 A1* | 10/2008 | Yoshida | A61B 8/469 600/443 |
| 2009/0175597 A1 | 7/2009 | Harada | |
| 2010/0195048 A1* | 8/2010 | Hammer | A61B 3/1025 351/206 |
| 2010/0302595 A1 | 12/2010 | Yamada et al. | |
| 2010/0312109 A1 | 12/2010 | Satoh | |
| 2011/0091083 A1 | 4/2011 | Liu et al. | |
| 2011/0137157 A1 | 6/2011 | Imamura et al. | |
| 2011/0267581 A1* | 11/2011 | Nakajima | A61B 3/102 351/206 |
| 2011/0277537 A1* | 11/2011 | Tsuzuki | A61B 5/082 73/23.3 |
| 2012/0063660 A1 | 3/2012 | Imamura et al. | |
| 2012/0130270 A1 | 5/2012 | Imamura et al. | |
| 2012/0194782 A1 | 8/2012 | Imamura | |
| 2013/0058553 A1 | 3/2013 | Yonezawa et al. | |
| 2014/0085606 A1 | 3/2014 | Miyasa et al. | |
| 2014/0240667 A1 | 8/2014 | Uji et al. | |
| 2014/0240668 A1 | 8/2014 | Uji et al. | |
| 2014/0240669 A1 | 8/2014 | Imamura | |

FOREIGN PATENT DOCUMENTS

| | | |
|---|---|---|
| CN | 102289805 A | 12/2011 |
| JP | 2005-270364 A | 10/2005 |
| JP | 2004-159767 A | 6/2006 |
| JP | 2007-252693 A | 10/2007 |
| JP | 2008-182544 A | 8/2008 |
| JP | 2009-183325 A | 8/2009 |
| JP | 2010-110656 A | 5/2010 |
| JP | 2011-010275 A | 1/2011 |
| JP | 2011-520503 A | 7/2011 |
| WO | 2005/086478 A1 | 9/2005 |
| WO | 2009/139722 A1 | 11/2009 |

OTHER PUBLICATIONS

Nov. 13, 2015 Chinese Official Action in Chinese Patent Appln. No. 201380010145.3.

* cited by examiner

F I G. 17
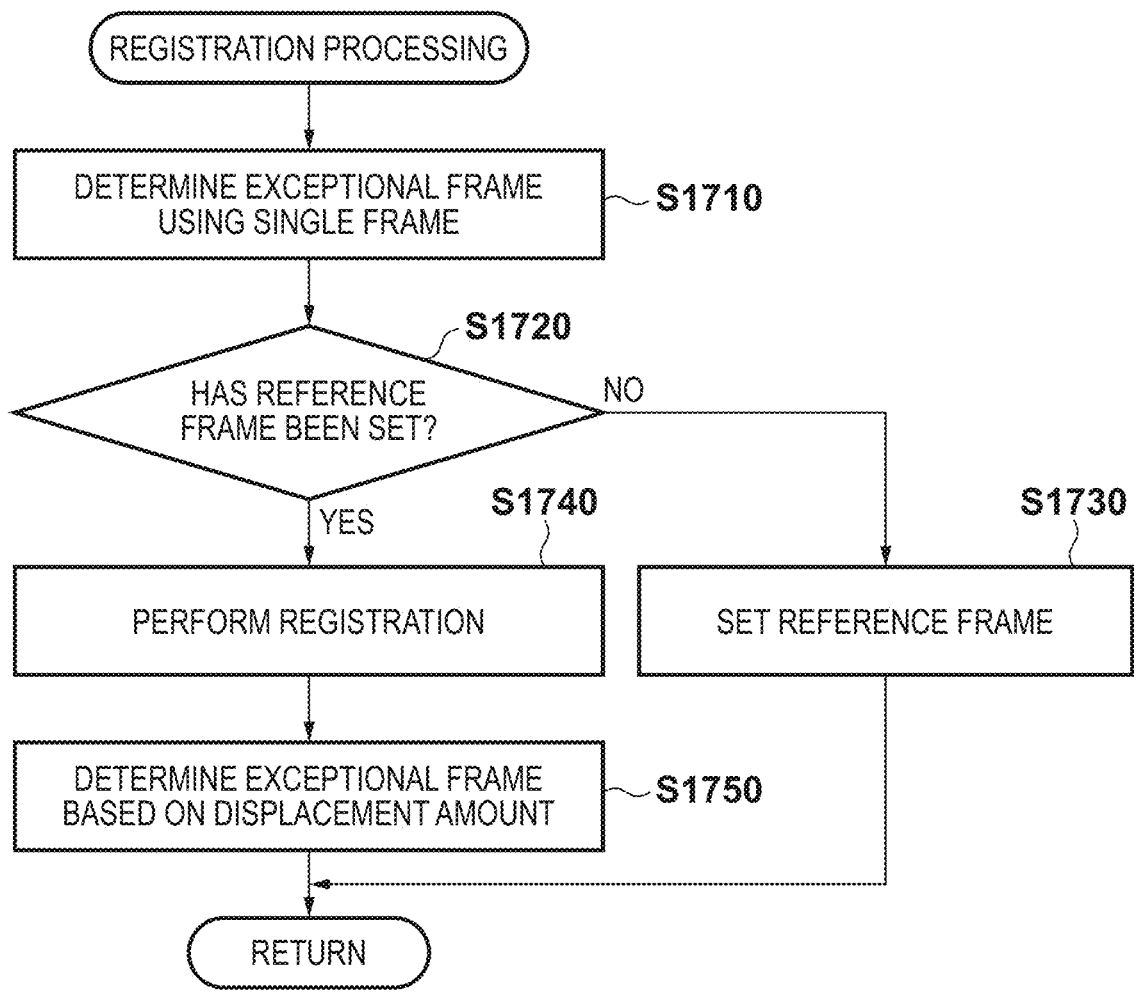

IMAGE FORMING APPARATUS AND IMAGE FORMING METHOD

TECHNICAL FIELD

The present invention relates to an image forming apparatus and image forming method and, more particularly, to an image forming apparatus and image forming method used for ophthalmic care.

BACKGROUND ART

Examination of an eye is widely performed for the purpose of preemptive medical care for lifestyle-related diseases and other diseases occupying major causes of blindness. A scanning laser ophthalmoscope (SLO) serving as an ophthalmic apparatus based on the principle of a confocal laser microscope performs raster scan on a fundus with a laser beam serving as measurement light, and quickly obtains a high-resolution planar image based on the light intensity of the return beam. Such an apparatus for capturing a planar image will be referred to as an SLO apparatus hereinafter. The planar image will be referred to as an SLO image hereinafter.

In recent years, it has become possible to obtain an SLO image of a retina with an improved lateral resolution by increasing the beam size of measurement light in an SLO apparatus. As the beam size of measurement light increases, however, the resolution and signal to noise ratio (SN ratio) of an SLO image decrease due to the aberration of an eye to be examined in obtaining an SLO image of a retina. To solve the problem, an adaptive optics SLO apparatus including adaptive optics for causing a wavefront sensor to measure the aberration of an eye to be examined in real time, and causing a wavefront correction device to correct the aberration of measurement light and its return beam occurring in the eye to be examined has been developed. Such an adaptive optics SLO apparatus can obtain a high-lateral resolution planar image.

It is possible to obtain such a high-lateral resolution SLO image as a moving image including a plurality of frames, as shown in FIG. 5A. To noninvasively observe hemodynamics, for example, a blood cell moving speed in a blood capillary and the like are measured after extracting retinal vessels from each frame (FIG. 5B). Furthermore, to evaluate the relationship with the visual function from the SLO image, photoreceptor cells are detected, and then their density distribution and arrangement are measured.

When observing/measuring blood cell kinetics, a change in blood vessel shape, and a change in the form of photoreceptor cells or the luminance in the SLO moving image, an exceptional frame where it is difficult to perceive/measure a target tissue, cell, or lesion due to differences in image features caused by an imaging apparatus or the influence of eye/eyelid movement may occur. For example, an area where observation/measurement processing is possible may become small for all frames (FIG. 5D) due to fixation disparity as shown in FIG. 5C, or low luminance frames (denoted by reference numeral 591 in FIG. 5E) may occur due to blinking. Alternatively, a moving image may include a frame with a low SN ratio due to the characteristics of an apparatus such as an aberration correction failure. In particular, since an SLO image of a diseased eye tends to include a frame influenced by blinking or fixation disparity, or an aberration correction SLO has a small field of view and is significantly influenced by small involuntary eye movement, it may be impossible to sufficiently obtain an area and the number of frames which are required to observe/measure a change with time by only performing inter-frame registration.

To prevent an exceptional frame as described above from occurring in an SLO moving image, there is provided a method of including, in an apparatus, a tracking function for preventing an exceptional frame from occurring in an imaging operation. It is, however, necessary to additionally provide an arrangement for capturing a wide field of view SLO image, and a complete tracking operation is actually difficult when small involuntary eye movement is large.

A technique is required in which when an exceptional frame occurs in an SLO moving image (FIG. 5C or 5E), the exceptional frame is determined and then deleted or corrected, thereby automatically forming an SLO moving image (FIG. 5A) where it is possible to observe or measure a target tissue, cell, or lesion.

Japanese Patent Laid-Open No. 2004-159767 (to be referred to as literature 1 hereinafter) describes, as a method of correctly associating the positions of the respective frames of a moving image of an eye to enable to observe/measure a target object, a technique of playing back a moving image having undergone registration for each frame in order to readily see the flow of a fluorescent agent flowing through an artery of the fundus. Japanese Patent Laid-Open No. 2010-110656 (to be referred to as literature 2 hereinafter) describes a method of detecting blinking or fixation disparity based on the similarity between OCT tomograms (still images).

Literature 1, however, considers only a case in which a moving image blurs due to movement of the fundus. Literature 1, therefore, describes only inter-frame registration, and does not describe a method of determining and excluding an exceptional frame (especially, a frame influenced by movement large enough so that it is impossible to observe a measurement range). Furthermore, literature 2 does not describe a method of detecting blinking or fixation disparity in a high-resolution planar image, or a technique (imaging/frame selection technique) of obtaining a moving image without any frame influenced by blinking or fixation disparity.

SUMMARY OF INVENTION

An embodiment of the present invention has been made in consideration of the above problems, and enables to generate, based on a moving image of the fundus, a moving image suitable for ophthalmic care or the like.

According to one aspect of the present invention, there is provided an image forming apparatus, comprising: determination means for determining an exceptional frame of a plurality of frames of a moving image of an eye based on an image feature of each frame; and generation means for generating a new moving image by extracting a frame sequence including frames extracted not to include the exceptional frame determined by the determination means.

According to another aspect of the present invention, there is provided an image forming apparatus for a moving image of an eye, comprising: determination means for determining an exceptional frame of an obtained moving image based on a displacement amount with respect to a reference area of the moving image; and change means for changing a moving image forming method based on the exceptional frame determined by the determination means.

According to another aspect of the present invention, there is provided an image forming method for an image forming apparatus, comprising the steps of: determining an exceptional frame of a plurality of frames of a moving image of an eye based on an image feature of each frame; and generating a new moving image by extracting a frame sequence including frames extracted not to include the exceptional frame determined in the step of determining.

According to another aspect of the present invention, there is provided an image forming method for an image forming apparatus for a moving image of an eye, comprising the steps of: determining an exceptional frame of an obtained moving image based on a displacement amount with respect to a reference area of the moving image; and changing a moving image forming method based on the exceptional frame determined in the step of determining.

Further features of the present invention will become apparent from the following description of exemplary embodiments with reference to the attached drawings.

BRIEF DESCRIPTION OF DRAWINGS

FIG. 17 is a flowchart illustrating processing in step S1620 according to the fourth embodiment.

DESCRIPTION OF EMBODIMENTS

Preferred embodiments of an image forming apparatus and a method according to the present invention will be described in detail below with reference to the accompanying drawings. Note that the present invention is not limited to the following embodiments.

First Embodiment

In a single SLO moving image including a plurality of frames, the number of which is larger than that necessary for observation/measurement, an image forming apparatus according to the embodiment determines, in advance, an exceptional frame having a displacement amount with respect to a reference frame based on image features included in the SLO moving image. Note that the SLO moving image is a moving image obtained by performing an imaging operation by an SLO apparatus. A predetermined number (which is equal to that of frames to be formed) of frames are extracted from a longest continuous frame sequence without any determined exceptional frames, thereby forming an SLO moving image for observation/measurement.

More specifically, an SLO moving image D including a plurality of frames, the number of which is larger than that Tf of frames necessary for observation/measurement (frames to be formed), is captured. Exceptional frames $E_j$ (j=1, . . . , n1) are then determined based on the image features of the SLO moving image D. Note that the exceptional frames $E_j$ are frames where a variation in image characteristics caused by a difference in imaging conditions such as a difference in aberration correction position and the influence of eye/eyelid movement such as pulsation or blinking is found. A longest one (sub moving image S1) of frame sequences (to be referred to as sub moving images $S_k$ (k=1, . . . , n2) hereinafter) each including a plurality of continuous frames without any exceptional frames $E_j$ in the SLO moving image D is extracted to form a new SLO moving image.

As described above, it is possible to automatically form an SLO moving image which includes an area (size) and the number of frames (a length) necessary for observation/measurement, and is not influenced by a variation in image characteristics caused by a difference in imaging conditions such as a difference in aberration correction position and the influence of eye/eyelid movement such as pulsation or blinking.

Figure 2:
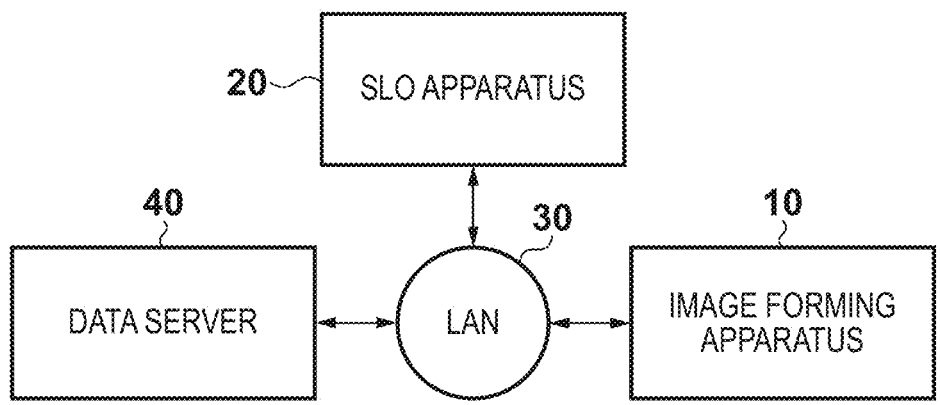
FIG. 2 is a block diagram showing an example of the configuration of an imaging system according to the first, second, or fourth embodiment.

FIG. 2 is a block diagram showing an example of the configuration of an imaging system including an image forming apparatus 10 according to the first embodiment. As shown in FIG. 2, the image forming apparatus 10 is connected with an SLO apparatus 20 and a data server 40 via a local area network (LAN 30) formed by an optical fiber, a USB, IEEE1394, or the like. Note that the apparatus 10 may be connected with these apparatuses via an external network such as the Internet. One apparatus may implement some of the image forming apparatus 10, SLO apparatus 20, and data server 40. For example, one information processing apparatus may include the image forming apparatus 10 and data server 40.

The SLO apparatus 20 serves as a scanning laser ophthalmoscope, and captures the planar image (SLO moving image) of a fundus region. The SLO apparatus 20 transmits, to the image forming apparatus 10 and data server 40, an SLO moving image D and information about a fixation target position F used to capture it. Note that the SLO apparatus 20 serves as an adaptive optics scanning laser ophthalmoscope (AO-SLO) which includes adaptive optics and performs aberration correction. The SLO apparatus 20 includes an SLD, a Shack-Hartmann wavefront sensor, adaptive optics, first and second beam splitters, an X-Y scanning mirror, a focusing lens, an aperture stop, an optical sensor, an image forming unit, and an output unit. Light emitted by the SLD (Super Luminescent Diode) serving as a light source is reflected by the fundus. Some of the reflected light is incident on the Shack-Hartmann wavefront sensor through the second beam splitter, and the remaining light is incident on the optical sensor through the first beam splitter. The Shack-Hartmann wavefront sensor is a device for measuring the aberration of an eye, and a CCD is connected to a lens array. When the incident light passes through the lens array, a luminescent spot group appears in the CCD, thereby measuring wave aberration based on misregistration of the projected luminescent spots. Based on the wave aberration measured by the Shack-Hartmann wavefront sensor, the adaptive optics drives an aberration correction device (a deformable mirror or spatial light phase modulator) to correct the aberration. The light having undergone the aberration correction enters the optical sensor through the focusing lens and aperture stop. It is possible to control a scanning position on the fundus by moving the X-Y scanning mirror, thereby obtaining data for a time (frame rate×number of frames) and an imaging target area designated in advance by an operator. The data is transmitted to the image forming unit, which forms image data (a moving image or still image) by correcting image distortion due to a variation in scanning speed or correcting luminance values. The output unit outputs the image data formed by the image forming unit. To focus on a specific depth position on the fundus, it is possible to perform at least one of adjustment using the aberration correction device of the adaptive optics and adjustment by arranging a focus adjustment lens (not shown) in the optics and moving the lens. Note that it is possible to use an ophthalmic apparatus such as a fundus camera including adaptive optics or an aberration correction device, instead of the SLO apparatus 20.

The data server 40 holds imaging condition data such as the SLO moving image D of the eye to be examined and the fixation target position F, and the image features of the eye. That is, the data server 40 stores the SLO moving image D and fixation target position F output from the SLO apparatus 20, and the image features of the eye output from the image forming apparatus 10. Furthermore, in response to a request from the image forming apparatus 10, the data server 40 transmits the SLO moving image D, the image features of the eye, and the normal value data of the image features to the image forming apparatus 10.

Figure 3:
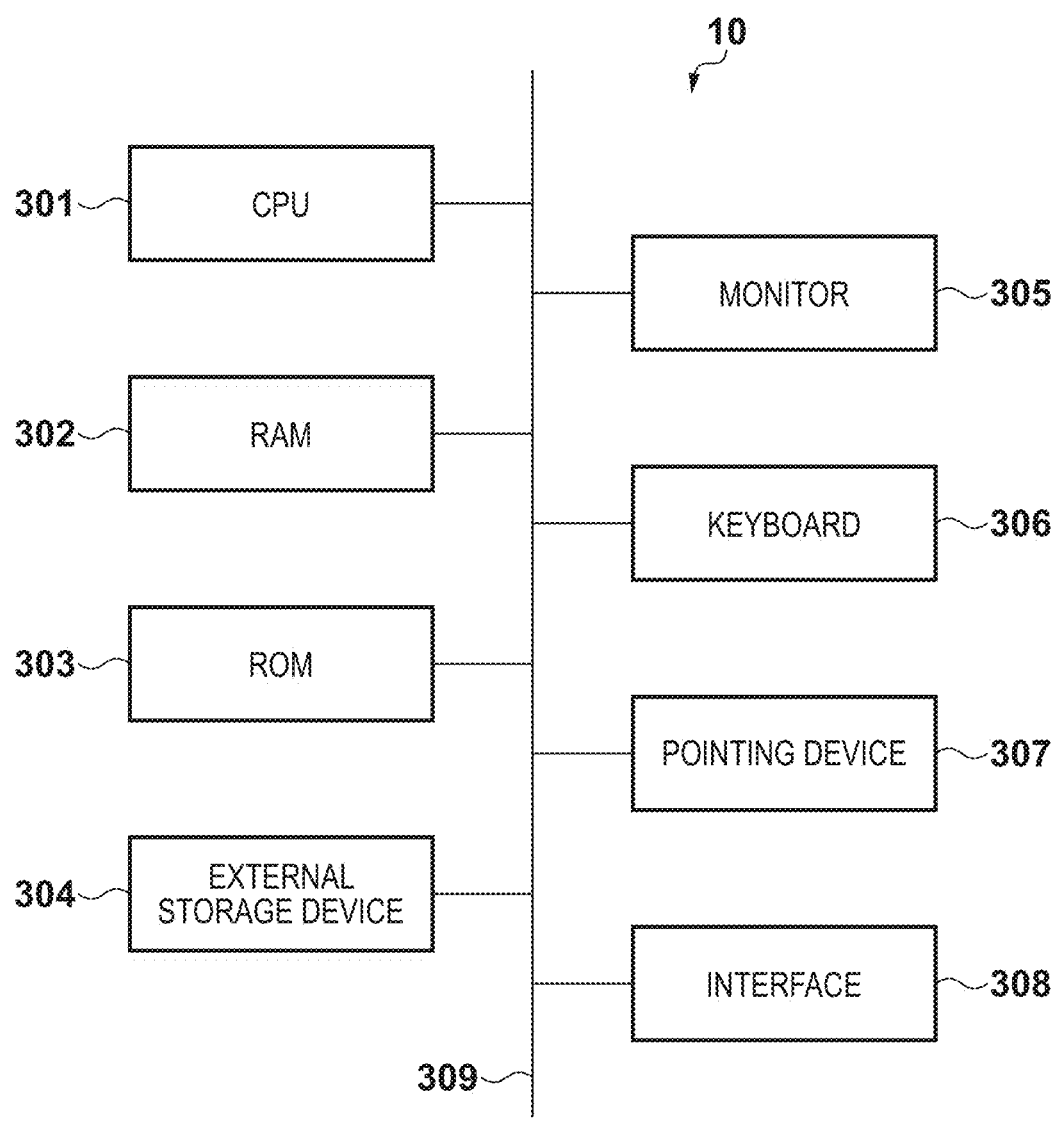
FIG. 3 is a block diagram showing an example of the hardware arrangement of a computer serving as the image forming apparatus according to the embodiment.

The hardware arrangement of the image forming apparatus 10 will be described with reference to FIG. 3. Referring to FIG. 3, reference numeral 301 denotes a central processing unit (CPU); 302, a memory (RAM); 303, a control memory (ROM); and 304, an external storage device. Furthermore, reference numeral 305 denotes a monitor; 306, a keyboard; 307, a pointing device (for example, a mouse); and 308, an interface for connecting to the LAN 30. The external storage device 304 stores control programs for implementing an image processing function according to the embodiment, and data to be used to execute the control programs. The control programs and data are loaded, as needed, into the RAM 302 via a bus 309 under the control of the CPU 301, and executed by the CPU 301, thereby functioning as each unit to be explained below.

Figure 1:
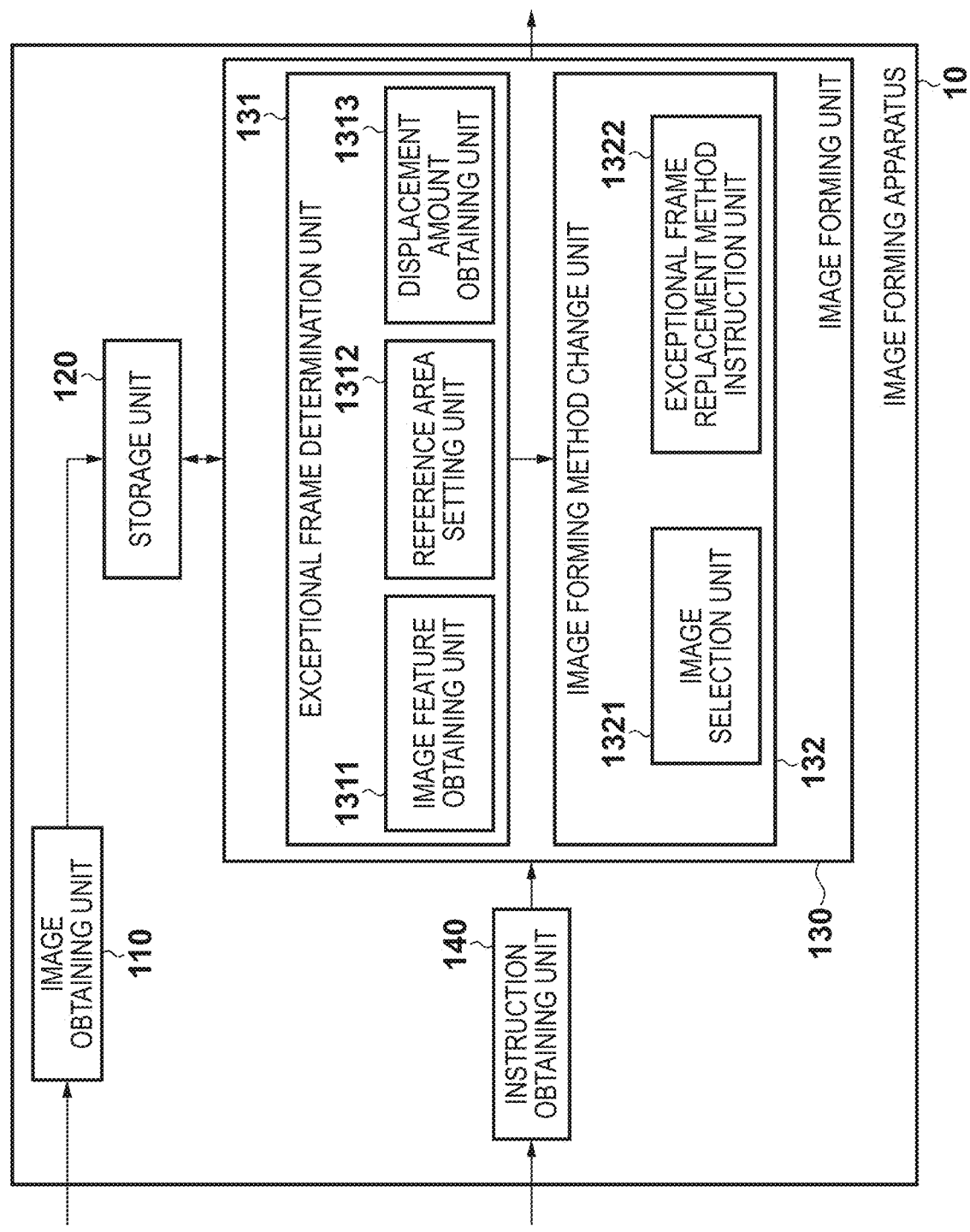
FIG. 1 a block diagram showing an example of the functional arrangement of an image forming apparatus according to the first embodiment.
Figure 4:
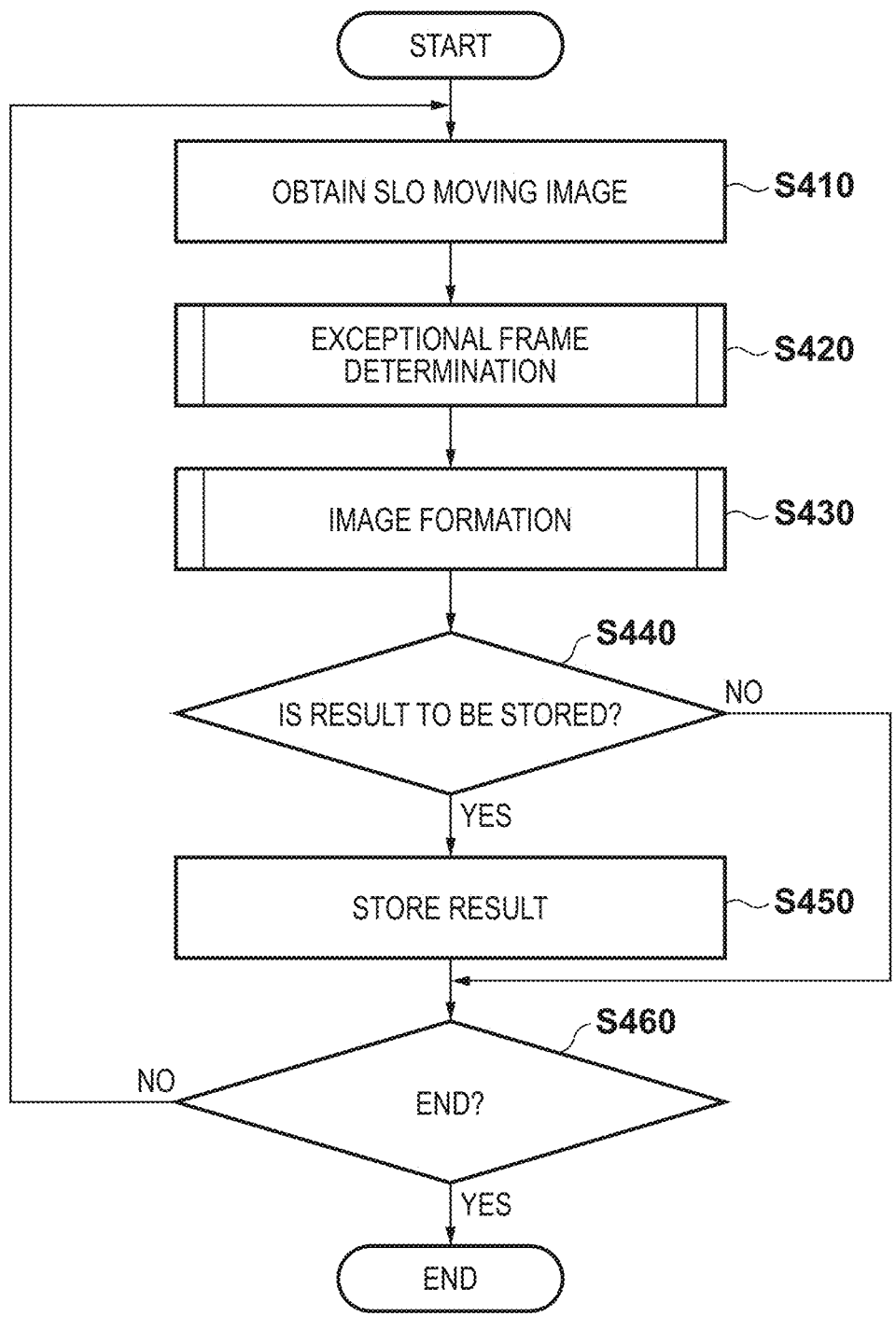
FIG. 4 is a flowchart illustrating processing executed by the image forming apparatus according to the first embodiment.

The functional arrangement of the image forming apparatus 10 according to the first embodiment will be described with reference to FIG. 1. FIG. 1 is a block diagram showing an example of the functional arrangement of the image forming apparatus 10. The image forming apparatus 10 includes an image obtaining unit 110, a storage unit 120, an image forming unit 130, and an instruction obtaining unit 140. The image forming unit 130 includes an exceptional frame determination unit 131 and an image forming method change unit 132. The exceptional frame determination unit 131 includes an image feature obtaining unit 1311, a reference area setting unit 1312, and a displacement amount obtaining unit 1313. The image forming method change unit 132 includes an image selection unit 1321 and an exceptional frame replacement method instruction unit 1322. The function of each block of the image forming apparatus 10 will be described below in association with the practical execution procedure of the image forming apparatus 10 shown in the flowchart of FIG. 4.

<Step S410> The image obtaining unit 110 requests the SLO apparatus 20 to obtain an SLO moving image D and fixation target position F. In this embodiment, the SLO apparatus 20 obtains the SLO moving image D by setting the fixation target position at the parafovea of a macular region. Note that in this embodiment, Tn represents the number of frames of an SLO moving image Df to be formed, and the number n0 of frames of the SLO moving image D is sufficiently larger than Tn. That is, even if the SLO moving image D has been influenced by small involuntary eye movement for a short time and blinking several times, the number of non-exceptional frames (normal frames) should be equal to or larger than Tn. Note that although the imaging position is set at the parafovea of the macular region, the present invention is not limited to this. The imaging position may be set at an arbitrary position.

In response to the obtaining request from the image obtaining unit 110, the SLO apparatus 20 obtains the SLO moving image D and the fixation target position F and transmits them. The image obtaining unit 110 receives the SLO moving image D and the fixation target position F from the SLO apparatus 20 via the LAN 30. The image obtaining unit 110 stores the received SLO moving image D and fixation target position F in the storage unit 120.

<Step S420> The exceptional frame determination unit 131 obtains image features from each frame Di (i=1, . . . , n0) of the SLO moving image D obtained by the image obtaining unit 110, and performs exceptional frame determination using the obtained image features. A frame with a smallest frame number among the frames other than exceptional frames is set as a reference frame. After that, exceptional frame determination is performed based on the interframe displacement amount of the image feature group obtained from each frame. The above-described practical exceptional frame determination processing will be explained in detail with reference to a flowchart shown in FIG. 6.

<Step S430> The image forming method change unit 132 obtains an exceptional frame number list from the exceptional frame determination unit 131. If there is no exceptional frame, the image forming unit 130 selects Tn frames from the beginning of the SLO moving image D, and adds an image header (attribute information) to the selected image to form an SLO moving image Df for observation/measurement. On the other hand, if an exceptional frame is included, the image forming method change unit 132 changes the image forming method, and the image forming unit 130 forms an SLO moving image Df for observation/measurement according to the changed image forming method. That is, the image forming unit 130 causes the image forming method change unit 132 to change the image forming method to generate a new moving image by extracting, from the SLO moving image D, a continuous frame sequence without any exceptional frame which has been determined by the exceptional frame determination unit 131 in step S420. Note that the practical procedure of the processing in step S430 will be described in detail with reference to flowcharts shown in FIGS. 7A and 7B.

<Step S440> The instruction obtaining unit 140 externally obtains an instruction indicating whether to store, in the data server 40, the SLO moving image D for observation/measurement which has been formed in step S430 and the fixation target position F. The operator inputs the instruction via, for example, the keyboard 306 or pointing device 307. If a storage operation is instructed, the process advances to step S450; otherwise, the process advances to step S460.

<Step S450> The image forming unit 130 transmits, to the data server 40, an examination date/time, information for identifying an eye to be examined, the SLO moving image Df, and the fixation target position F of the image group in association with each other.

<Step S460> The instruction obtaining unit 140 externally obtains an instruction indicating whether to terminate the forming processing of the SLO moving image Df by the image forming apparatus 10. The operator inputs the instruction via the keyboard 306 or pointing device 307. If the unit 140 obtains an instruction to terminate the processing, the analysis processing ends. On the other hand, if the unit 140 obtains an instruction to continue the processing, the process returns to step S410 to execute processing for a next eye to be examined (or re-execute processing for the same eye to be examined).

Figure 6:
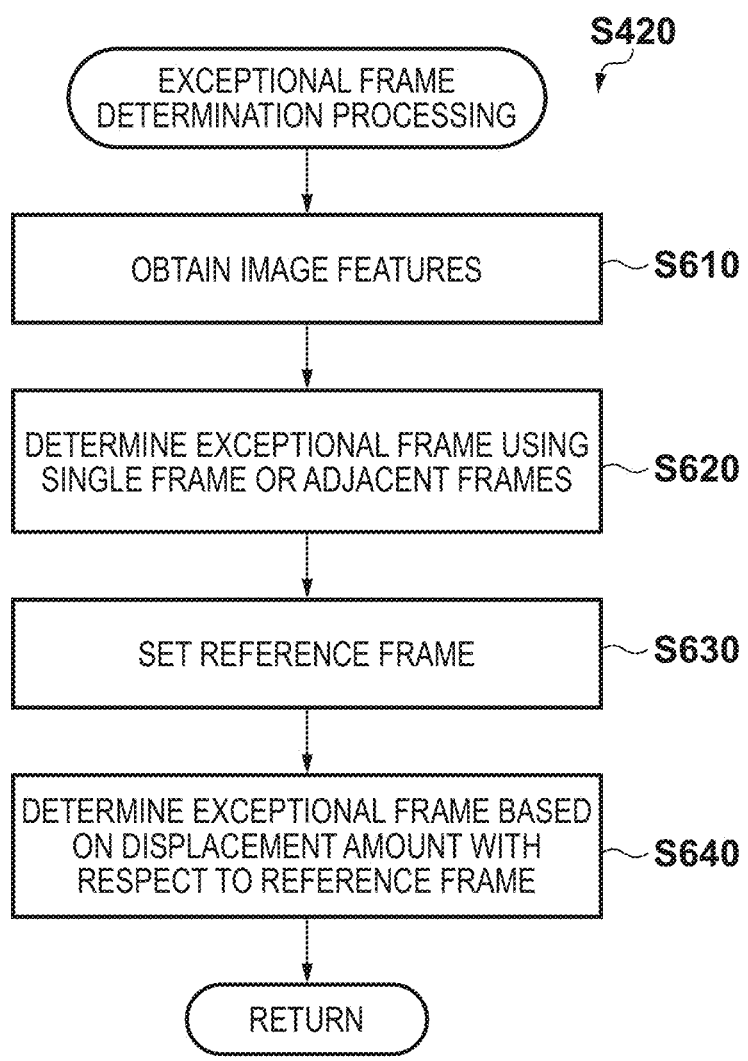
FIG. 6 is a flowchart illustrating processing in step S420 according to the first embodiment.

The exceptional frame determination processing executed in step S420 will now be described in detail with reference to FIG. 6.

<Step S610> The image feature obtaining unit 1311 obtains image features from the SLO moving image D. In this embodiment, the unit 1311 obtains, as image features, an average luminance value $A_i$, a signal to noise ratio (SN ratio), and a blood vessel area $V_i$ in each frame $D_i$ of the SLO moving image D. An arbitrary known blood vessel extraction method can be used as a blood vessel area obtaining method, and in this embodiment, an area where a luminance value is equal to or smaller than a threshold T1 is obtained. Furthermore, intersection portions $C_{in}$ (n=1, ..., n4≥3) of a sequence of points $B_{im}$ (m=1, 2, ..., n3) obtained by thinning the blood vessel area $V_i$ are also obtained. Note that feature amounts to be obtained are not limited to the above ones, and image features necessary for subsequent exceptional frame determination processing are obtained.

<Step S620> The exceptional frame determination unit 131 uses the image features obtained in step S610 to determine an exceptional frame based on the image features of a single frame and comparison with the image features of an adjacent frame. For example, the exceptional frame determination unit 131 detects, from each frame $D_i$ of the SLO moving image D, as an exceptional frame $E_j$, a frame where the luminance is extremely low due to blinking, a frame where image distortion has occurred due to small involuntary eye movement, or a frame where the SN ratio is low due to an aberration correction failure. In this embodiment, if the average luminance value $A_i$ of a frame $D_i$ is equal to or smaller than a threshold T2, it is considered that a luminance error has occurred due to blinking, thereby determining the frame as an exceptional frame $E_j$. If the difference, between adjacent frames, in value of the sum of squares of the distance between the blood vessel intersection portions $C_{in}$ of the frame $D_i$ is equal to or larger than a threshold T3, it is considered that image distortion has occurred due to small involuntary eye movement, thereby determining the frame $D_i$ as an exceptional frame. Furthermore, if the SN ratio of the frame $D_i$ is equal to or smaller than a threshold T4, it is considered that an aberration correction failure has occurred, thereby determining the frame $D_i$ as an exceptional frame.

Note that the exceptional frame determination method in steps S610 and S620 is not limited to the above one, and an arbitrary exception determination method may be used instead of or in addition to the above-described determination method. For example, the luminance statistic (average value, mode, or maximum value) of a differential image obtained by executing differential processing for each frame is calculated. If the luminance statistic is equal to or smaller than a threshold T5, it may be considered that the frame blurs due to movement of an object, thereby determining the frame as an exceptional frame.

<Step S630> The reference area setting unit 1312 sets a reference area for determining a fixation disparity frame (exceptional frame) in the moving image D. In this embodiment, the unit 1312 sets, as a reference frame, a frame with a smallest frame number among frames other than those which have been determined as exceptional frames in step S620, and sets, as a reference area, the whole or part of the reference frame.

Note that the reference area setting method is not limited to this, and an arbitrary setting method may be used. For example, the unit 1312 may obtain a reference frame number specified by the user from the instruction obtaining unit 140, and set the whole reference frame as a reference area. Alternatively, the unit 1312 may set, as a reference area, an area designated by the user (an area designated by the user within the frame designated by the user). Alternatively, the image feature obtaining unit 1311 may use an arbitrary known image processing method to detect a specific part (central fovea) or lesion, and then the unit 1312 may set, as a reference area, the part or lesion area detected in a non-exceptional frame with a smallest frame number.

<Step S640> The displacement amount obtaining unit 1313 calculates a displacement amount between an image feature (the blood vessel intersection portion $C_{in}$) in the reference frame set in step S630 and that in a non-reference frame, and then determines, as an exceptional frame, a frame where the displacement amount is larger than a tolerance value. In this embodiment, as the displacement amount of a given frame with respect to the reference frame, a displacement amount vector (x, y, θ, sx, sy) having, as its components, a translation (x, y), rotation θ, and magnification (sx, sy) is defined. If at least one of x>Tx, y>Ty, θ>Tθ, sx>Tsx, and sy>Tsy holds, the given frame is determined as an exceptional frame (Tx, Ty, Tθ, Tsx, and Tsy are respectively predetermined thresholds).

Note that the definition of the displacement amount is not limited to this, and an arbitrary value may be used as long as it represents the degree of displacement (scalar quantity or vector quantity). A proportion of the reference area to be observed/measured which is included in each frame (for example, (area of whole reference area)/(area of reference area included in each frame $D_i$)) may be defined as a displacement amount.

Figure 7A:
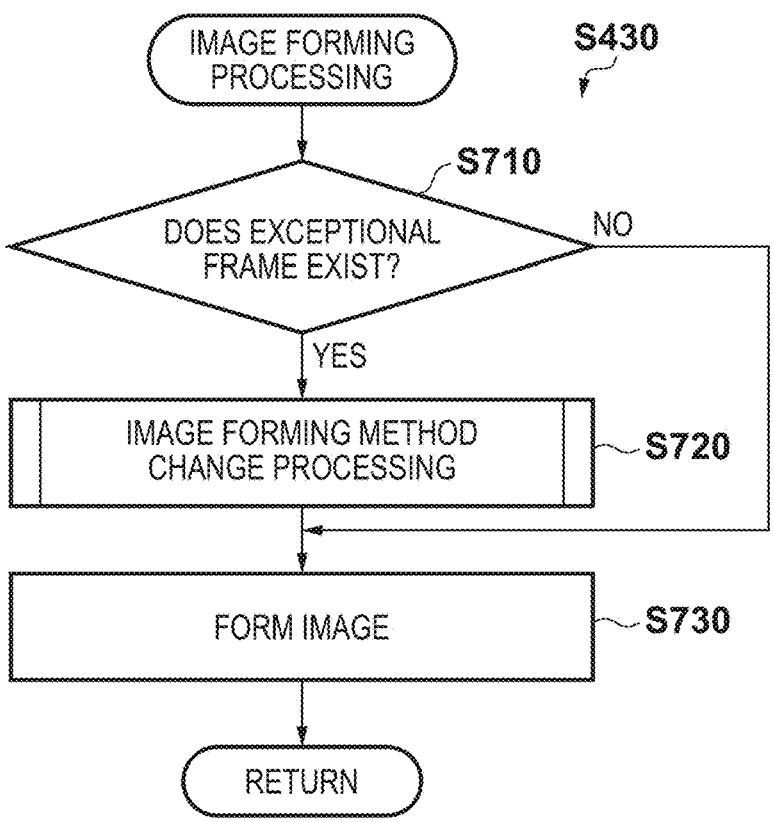
FIGS. 7A and 7B are flowcharts illustrating processing in step S430 according to the first embodiment.

The processing executed in step S430 will be described in detail with reference to FIG. 7A.

<Step S710> The image forming method change unit 132 obtains an exceptional frame number list included in the SLO moving image D from the exceptional frame determination unit 131. If the exceptional frame list is empty (there is no exceptional frame), the process advances to step S730. If one or more exceptional frames exist, the process advances to step S720.

<Step S720> The image forming method change unit 132 calculates a frame count Nsk of a sub moving image Sk without any exceptional frames of the SLO moving image D, and then calculates a maximum value Nsl of Nsk. If the maximum value Nsl≥Tn, the image forming method change unit 132 selects a longest sub moving image Sl among the sub moving images Sk, thereby redefining a new SLO moving image D. On the other hand, if the maximum value Nsl<Tn, the image forming method change unit 132 instructs the image forming unit 130 to replace exceptional frames by performing interpolation processing for an exceptional frame sequence adjacent to the sub moving image Sl using the preceding and succeeding sub moving images. A longest sub moving image defined by this instruction is set as a new SLO moving image D, and the process advances to step S730. Note that details of the processing executed by the image forming method change unit 132 in step S720 will be described later with reference to the flowchart shown in FIG. 7B.

<Step S730> The image forming unit 130 selects Tn frames from the beginning of the SLO moving image D defined in step S720, and adds an image header (attribute information) to form an SLO moving image Df for observation/measurement. If it has been instructed to replace the exceptional frames by performing image interpolation in step S720, the image forming unit 130 replaces the exceptional frames using the instructed image interpolation method to form an SLO moving image Df.

Figure 7B:
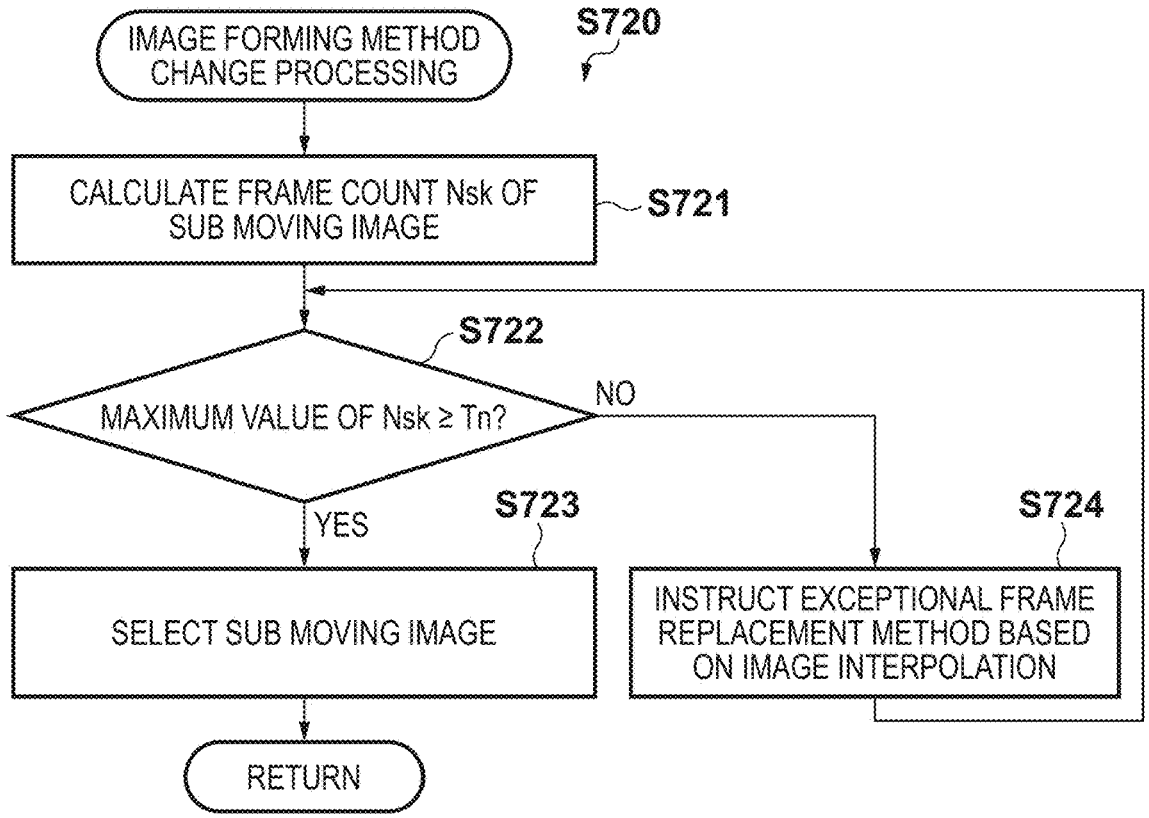

The processing executed in step S720 will be described in detail with reference to FIG. 7B.

<Step S721> The image forming method change unit 132 obtains an exceptional frame number list from the exceptional frame determination unit 131, and calculates the maximum value Nsl of the length Nsk of a frame sequence (sub moving image Sk) which is included in the SLO moving image D and includes continuous frames without any exceptional frames.

<Step S722> If Nsl≥Tn, the process advances to step S723; otherwise, the process advances to step S724.

<Step S723> The unit 132 selects a longest frame sequence (sub moving image Sl) from the SLO moving image D, and redefines it as a new SLO moving image D.

<Step S724> If the longest continuous frame sequence does not include the predetermined number (Tn) of frames, the image forming unit 130 generates an interpolation frame using the preceding and succeeding non-exceptional frames of a frame which has been determined as an exceptional frame. The image forming unit 130 generates a continuous frame sequence including the predetermined number of frames using the generated interpolation frame as a non-exceptional frame. For example, the image forming unit 130 replaces an exceptional frame sequence adjacent to the longest sub moving image Sl of the SLO moving image D by executing image interpolation processing using the preceding and succeeding sub moving images of the exceptional frame sequence, and recalculates Nsl. Although a linear interpolation method is used as an image interpolation method in this embodiment, the interpolation method is not limited to this and an arbitrary known image interpolation method may be used. By repeating the interpolation processing (step S724) until Nsl≥Tn holds, an obtained longest sub moving image Sl' is redefined as a new SLO moving image D.

Note that in this embodiment, the image interpolation processing is executed when the maximum value Nsl of the frame count Nsk of the sub moving image Sk is smaller than Tn. The present invention, however, is not limited to this. For example, if Nsl<Tn, the processing of forming an SLO moving image Df may be terminated, and a message to perform an imaging operation again may be displayed on a display unit (not shown).

If a tolerance value is set for the number of frames to be interpolated, and it is necessary to interpolate the number of frames exceeding the tolerance value in step S724, a warning may be displayed on the display unit (not shown), thereby terminating the processing of forming the SLO moving image Df.

Although the frame count of the SLO moving image Df to be formed is a constant value (Tn) in this embodiment, the present invention is not limited to this. In step S723 or S730, for example, the longest sub moving image Sl may be redefined as a new SLO moving image D intact, and an image header may be added to form an SLO moving image Df for observation/measurement. If it is possible to obtain a plurality of frame sequences each including the number of frames equal to or larger than the constant value (Tn), a frame sequence, among the plurality of frame sequences, for which the statistic of a displacement amount between the frames of the frame sequence is smallest may be selected.

As described above, according to the first embodiment, the image forming apparatus 10 determines an exceptional frame of the SLO moving image D based on image features, and forms an SLO moving image Df based on a longest continuous frame sequence without any determined exceptional frames. With this arrangement, it is possible to automatically form an SLO moving image Df which includes an area (spatial size) and the number of frames (time length) necessary for observation/measurement, and is not influenced by a variation in image characteristics caused by a difference in imaging conditions such as a difference in aberration correction position and eye/eyelid movement such as pulsation or blinking.

Second Embodiment

In the second embodiment, a registration unit 134 determines an exceptional frame based on the image features of a single frame, and performs inter-frame registration for a moving image from which the exceptional frames have been excluded. After the registration, an exceptional frame is determined based on differences in image features between frames. According to the arrangement of the second embodiment, it is possible to more correctly calculate a displacement amount with respect to a reference frame, and determine an exceptional frame, thereby enabling to automatically form an SLO moving image Df for observation/measurement including a necessary area and a necessary number of frames.

Figure 8:
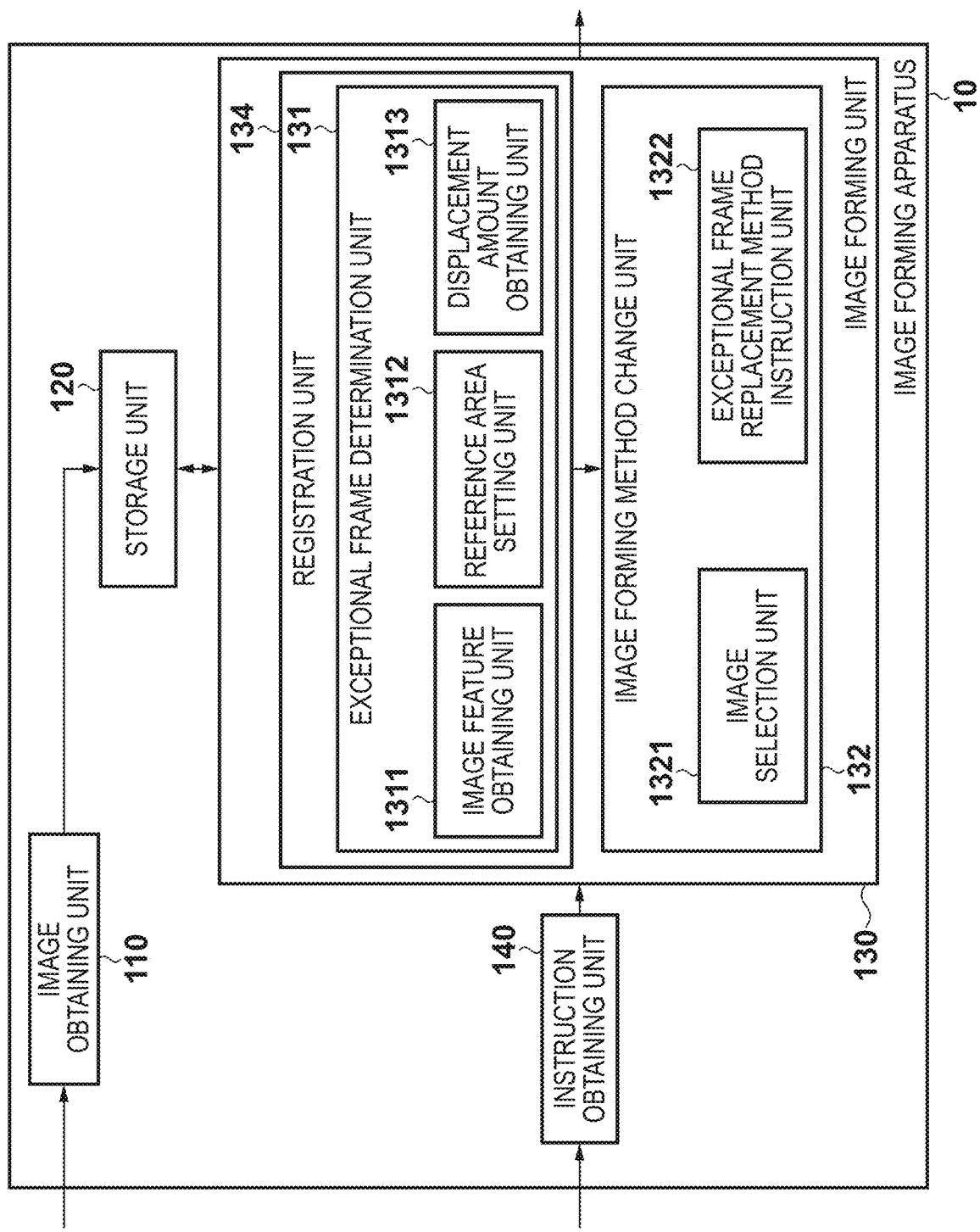
FIG. 8 is a block diagram showing an example of the functional arrangement of an image forming apparatus according to the second embodiment.
Figure 9:
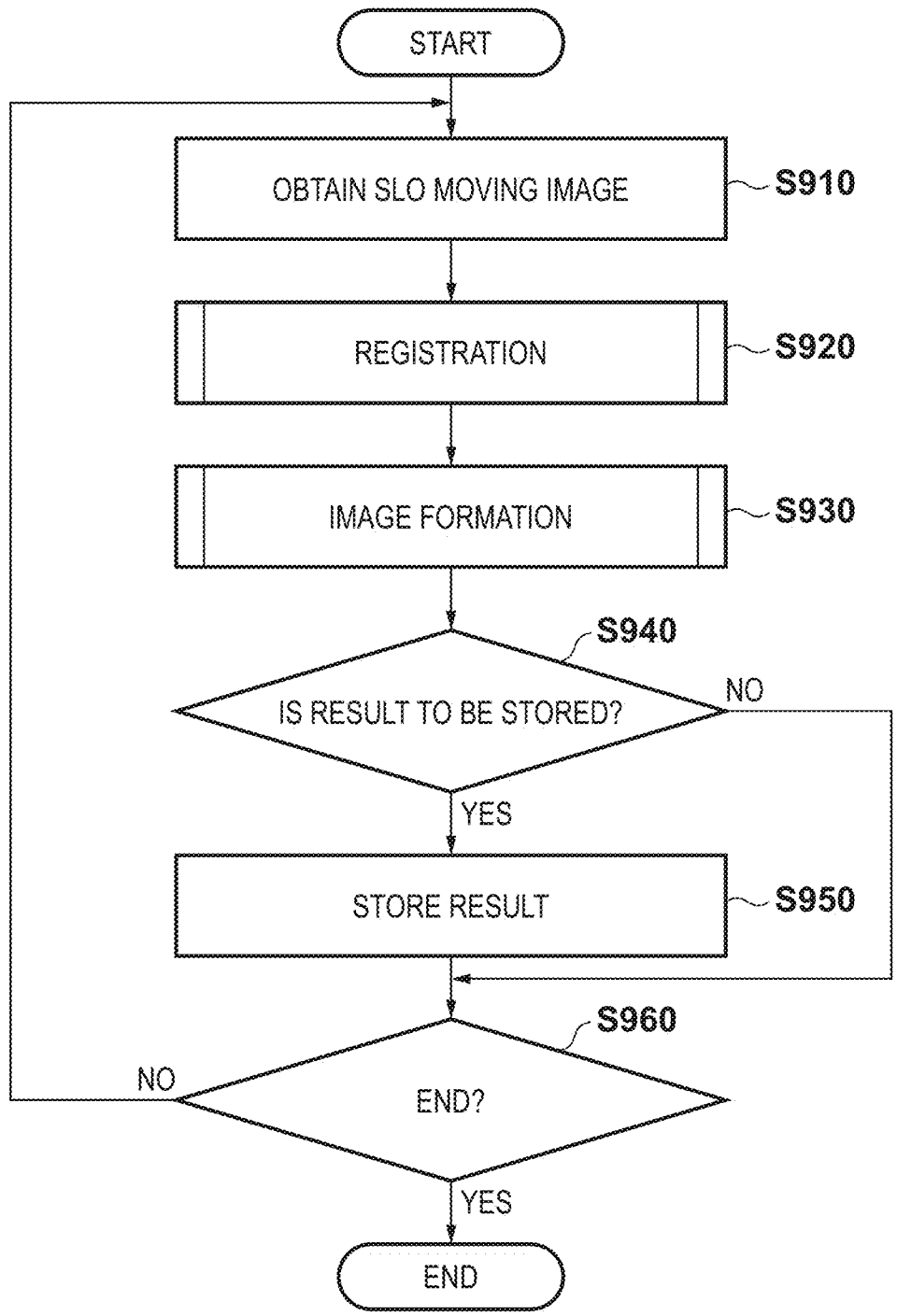
FIG. 9 is a flowchart illustrating processing executed by the image forming apparatus according to the second embodiment.

FIG. 8 shows an example of the functional arrangement of an image forming apparatus 10 according to the second embodiment. The arrangement in the second embodiment is different from that in the first embodiment (FIG. 1) in that an image forming unit 130 includes the registration unit 134, and the registration unit 134 includes an exceptional frame determination unit 131. Image forming processing according to the second embodiment will be described below with reference to a flowchart shown in FIG. 9. Note that operations in steps except for step S920 in FIG. 9 are the same as those in the first embodiment (FIG. 4) (that is, operations in steps S910 and S930 to S960 are the same as those in steps S410 and S430 to S460). In the second embodiment, therefore, processing in step S920 will be described.

Figure 10:
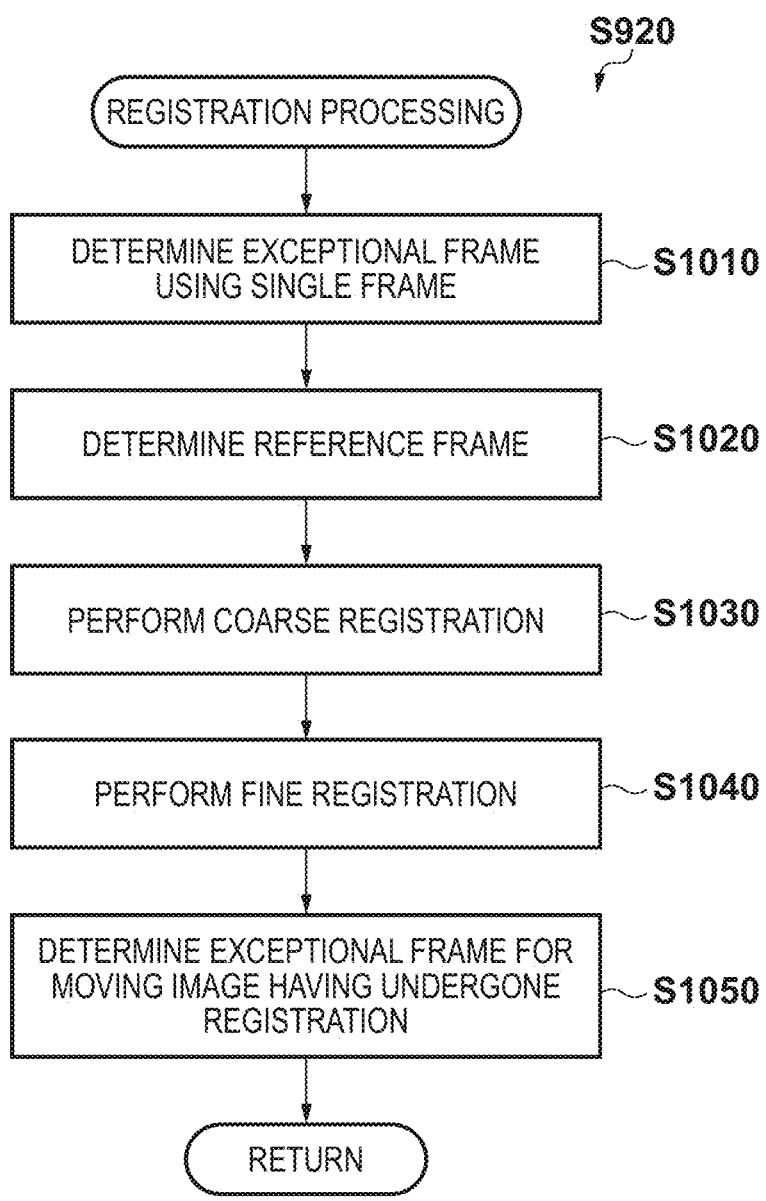
FIG. 10 is a flowchart illustrating processing in step S920 according to the second embodiment.

<Step S920> The registration unit 134 reads an SLO moving image D from a storage unit 120, and performs inter-frame registration for the SLO moving image D. Note that the inter-frame registration indicates adjustment such that the images of adjacent frames are at the same position, and is implemented by a well-known technique. The registration processing executed in step S920 will now be described with reference to a flowchart shown in FIG. 10.

<Step S1010> The exceptional frame determination unit 131 performs exceptional frame determination using a single frame (exceptional frame determination using the image features of a single frame) for each frame of the SLO moving image D. In this embodiment, an image feature obtaining unit 1311 calculates an average luminance value $A_i$ and an SN ratio $SN_i$ of each frame. The exceptional frame determination unit 131 determines that a luminance error has occurred if $A_i$ is equal to or smaller than a threshold T2, and determines that the frame has low image quality if the SN ratio $SN_i$ is equal to or smaller than a threshold T4, thereby determining the frame as an exceptional frame. Note that the exceptional frame determination method using the image features of a single frame is not limited to this, and an arbitrary exception determination method may be used.

<Step S1020> The registration unit 134 sets a reference frame as a registration reference. In this embodiment, a frame with a smallest frame number among frames other than those which have been determined as exceptional frames in step S1010 is set as a reference frame. Note that the reference frame setting method is not limited to this, and an arbitrary setting method may be used. For example, the unit 134 may obtain a reference frame number specified by the user from an instruction obtaining unit 140, and set, as a reference frame, a frame corresponding to the specified reference frame number.

<Step S1030> The registration unit 134 roughly associates the positions of frames with each other (coarse registration). Although an arbitrary registration method can be used, coarse registration is performed using a correlation coefficient as an inter-image similarity evaluation function and using affine transformation as a coordinate transformation method in this embodiment. Note that frames to undergo coarse registration in step S1030 and fine registration in step S1040 are those which have not been determined as exceptional frames in step S1010.

<Step S1040> The registration unit 134 performs fine registration based on data of the coarse position correspondence between frames obtained in step S1030. In this embodiment, the unit 134 performs fine registration between frames using an FFD (Free Form Deformation) method as a non-rigid registration method for the moving image which has undergone coarse registration in step S1030. Note that the fine registration method is not limited to this, and an arbitrary registration method may be used.

<Step S1050> The exceptional frame determination unit 131 performs exceptional frame determination based on differences in image features between frames for each frame of the moving image which has undergone fine registration in step S1040. In this embodiment, a reference area setting unit 1312 sets a reference frame, and a displacement amount obtaining unit 1313 calculates the difference between the reference frame and each frame (except for the reference frame), thereby obtaining the histogram of a difference image. If the average value of the histogram is equal to or larger than a threshold T6 and the variance of the histogram is equal to or larger than a threshold T7, the exceptional frame determination unit 131 determines that a different position on the fundus is temporarily captured due to small involuntary eye movement, thereby determining the frame as an exceptional frame.

Note that the exceptional frame determination method using differences in image features between frames is not limited to this, and an arbitrary determination method may be used. For example, for each frame of the moving image having undergone fine registration, extraction of a blood vessel and detection of a blood vessel intersection portion $C_{in}$ are performed as in the first embodiment. The sum of squares of the distance between the blood vessel intersection portions $C_{in}$ is obtained in each frame. If the difference in value of the sum of squares of the distance between adjacent frames is equal to or larger than a threshold T3, it is considered that image distortion has occurred, thereby determining the frame as an exceptional frame.

In this embodiment, a combination of registration parameters with which the whole frame of the SLO moving image D is most similar to the reference frame is obtained using pixel value-based inter-image similarity. The present invention, however, is not limited to this. For example, image features (a part such as a lesion or central fovea, and a feature point such as a branch of a blood vessel) to be observed may be detected in each frame of the SLO moving image D, and frames of the SLO moving image may undergo registration so that the positions of the image features most finely coincide with each other. Furthermore, image features obtained in inter-frame registration may be used for exceptional frame determination, and image features obtained for exceptional frame determination may be used in inter-frame registration. In this way, commonly using the image features in exceptional frame determination and inter-frame registration can improve the processing efficiency.

As described above, according to the second embodiment, the image forming apparatus 10 performs inter-frame registration after excluding exceptional frames. This prevents registration from being executed for frames (exceptional frames) which need not undergo registration. In inter-frame registration, it is possible to exclude the influence of small involuntary eye movement, blinking, or the like. Furthermore, since exceptional frame determination using a reference frame is performed after registration, it is possible to more correctly calculate a displacement amount with respect to the reference frame, and determine an exceptional frame. This enables to automatically form an SLO moving image Df including a necessary number of frames and an area appropriate for observation/measurement.

Third Embodiment

Figure 11:
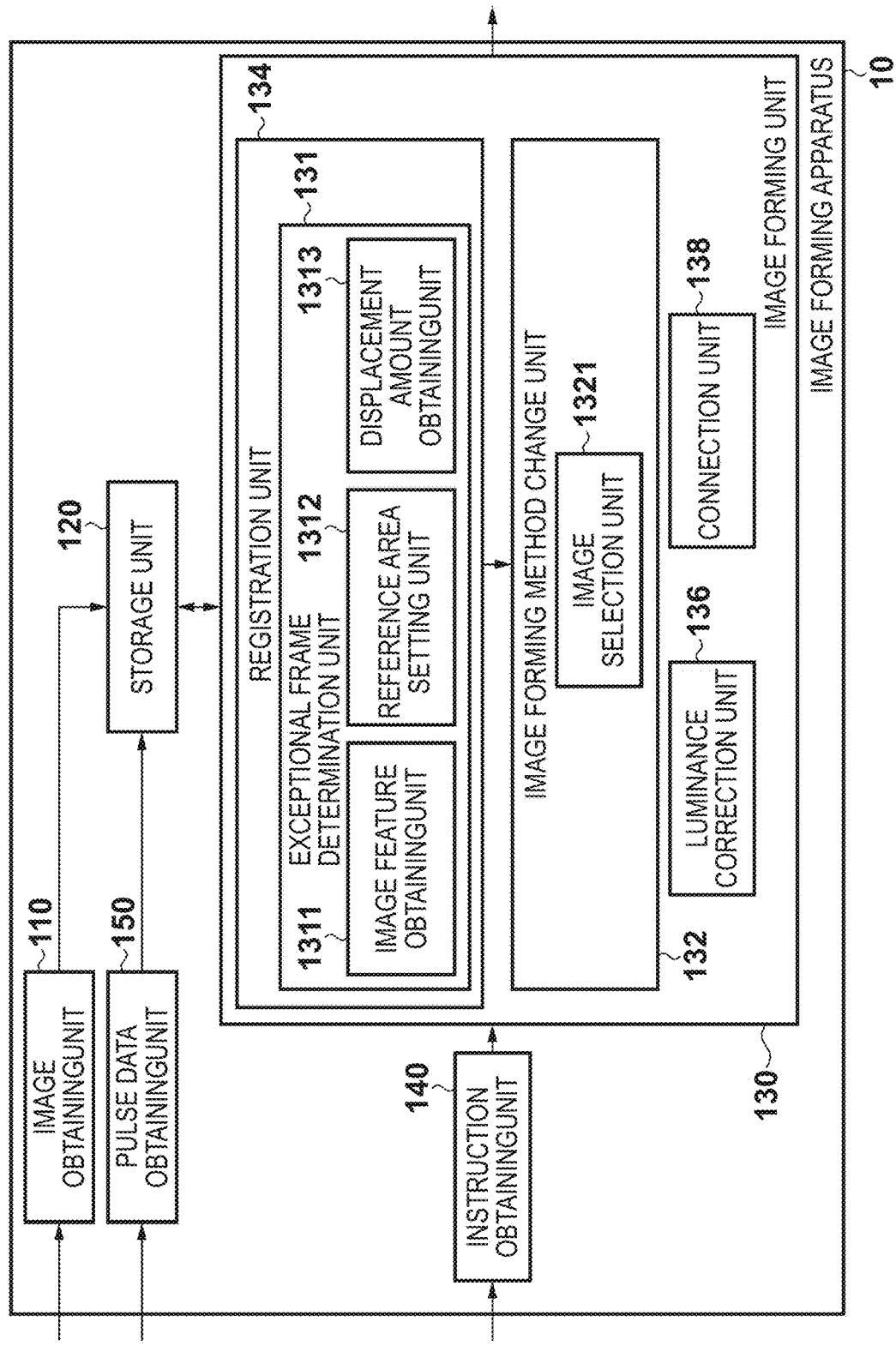
FIG. 11 is a block diagram showing an example of the functional arrangement of an image forming apparatus according to the third embodiment.

FIG. 11 is a block diagram showing an example of the functional arrangement of an image forming apparatus 10 according to the third embodiment. The image forming apparatus 10 of the third embodiment is different from that of the second embodiment (FIG. 8) in that a pulse data obtaining unit 150 is provided, an image forming method change unit 132 does not include the exceptional frame replacement method instruction unit 1322, and a luminance correction unit 136 and connection unit 138 are additionally included. More specifically, an image obtaining unit 110 repeatedly captures an SLO moving image at the same imaging position (SLO moving images $D_n$ (n=1, 2, ..., n5)), and at the same time, the pulse data obtaining apparatus 150 obtains biological signal data (pulse data) like a pulse wave as phase data $P_n$. The luminance correction unit 136 extracts a longest frame sequence (sub moving image $S_{nl}$)

from each SLO moving image Dn, and adjusts the luminance between the sub moving images Snl. Furthermore, the connection unit 138 connects the sub moving images Snl having undergone luminance adjustment with reference to the pulse data Pn, thereby forming an SLO moving image Df including an area and the number of frames necessary for observation/measurement. With this arrangement, it is possible to automatically form an SLO moving image Df which includes a necessary area (spatial size) and can be observed/measured for a longer time.

Figure 12:
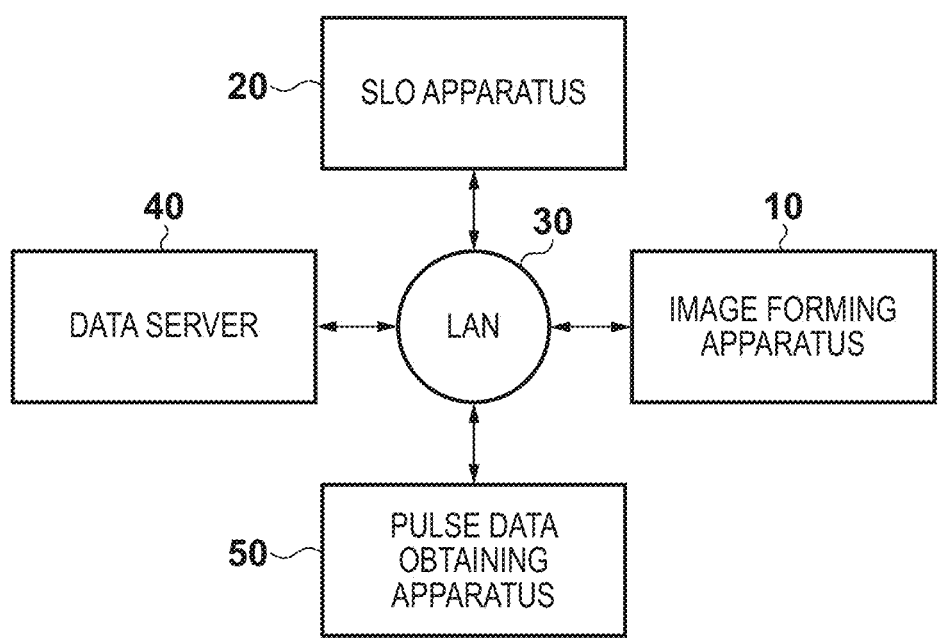
FIG. 12 is a block diagram showing an example of the configuration of an imaging system according to the third embodiment.

FIG. 12 shows an example of the configuration of an imaging system according to this embodiment. The imaging system in the third embodiment is different from that in the second embodiment (FIG. 2) in that a pulse data obtaining apparatus 50 is connected to a LAN 30. The pulse data obtaining apparatus 50 is used to obtain biological signal data (pulse data) which autonomously changes, and includes, for example, a sphygmograph or electrocardiograph. In this embodiment, a sphygmograph is used. In response to an operation by an operator (not shown), the pulse data obtaining apparatus 50 obtains pulse data Pn as well as the SLO moving image Dn, and transmits the obtained pulse data Pn to the image forming apparatus 10 and a data server 40.

The procedure of image forming processing according to the third embodiment is as shown in FIG. 9. Operations in steps except for steps S910, S920, and S930 are the same as those in the second embodiment. Processing in steps S910, S920, and S930 will be described below.

<Step S910> An image obtaining unit 110 requests an SLO apparatus 20 to obtain SLO moving images Dn obtained by performing an imaging operation several times within the same examination, and a fixation target position F. In this embodiment, the fixation target position is set at the parafovea of a macular region to obtain the SLO moving images Dn. Note that in this embodiment, Tn represents the number of frames of an SLO moving image Df to be finally formed. The imaging position and the imaging position setting method are not limited to them, and the imaging position may be set at an arbitrary position.

In response to the obtaining request output from the image obtaining unit 110, the SLO apparatus 20 obtains the SLO moving images Dn and fixation target position F, and transmits them. The image obtaining unit 110 receives the SLO moving images Dn and fixation target position F from the SLO apparatus 20 via the LAN 30. The image obtaining unit 110 stores the received SLO moving images Dn and fixation target position F in a storage unit 120.

<Step S920> A registration unit 134 reads the SLO moving images Dn from the storage unit 120, and performs inter-frame registration for the SLO moving images Dn. In this embodiment, a reference frame setting method is different from that in the second embodiment, and a reference frame in an SLO moving image D1 captured first is used as a reference frame for registration in other SLO moving images D2 to Dn.

Note that the reference frame setting method is not limited to this, and an arbitrary setting method may be used. For example, the following setting method may be used.

Process P1: Inter-frame registration is performed for each SLO moving image Dn by the same method as that in the second embodiment, and exceptional frame determination is performed.

Process P2: After process P1, a reference frame in an SLO moving image Dn including a smallest number of exceptional frames is set as a reference frame in other SLO moving images.

Process P3: For other SLO moving images, registration processing is performed again using the reference frame set in process P2.

<Step S930> The image forming method change unit 132 obtains an exceptional frame number list for each SLO moving image Dn from an exceptional frame determination unit 131. If there is no exceptional frame in each SLO moving image Dn, based on the pulse data Pn obtained from the pulse data obtaining unit 150 an image forming unit 130 selects a largest number of frames in cycles of the pulse data from the phase of the pulse data designated in advance, thereby generating a sub moving image Snl. The unit 130 then connects the sub moving images Snl based on imaging times in chronological order. If the number of frames of the connected moving images is equal to or larger than Tn, the unit 130 extracts Tn frames from the beginning of the connected moving images, and adds an image header (attribute information), thereby forming an SLO moving image Df for observation/measurement. If the number of frames of the connected moving images is smaller than Tn, the unit 130 displays a warning to perform an imaging operation again or continue the imaging operation. On the other hand, if the SLO moving image Dn includes an exceptional frame, the image forming method change unit 132 changes the image forming method to include no exceptional frame, and forms an SLO moving image Df for observation/measurement.

Figure 13:
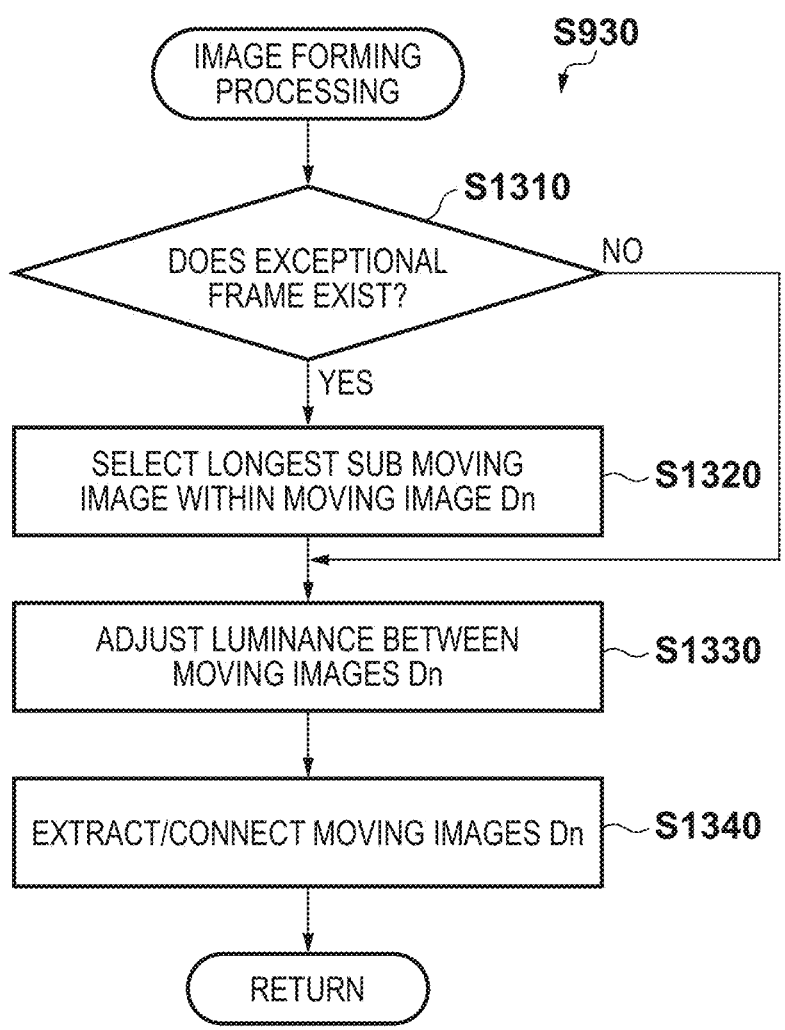
FIG. 13 is a flowchart illustrating processing in step S930 according to the third embodiment.
Figure 14:
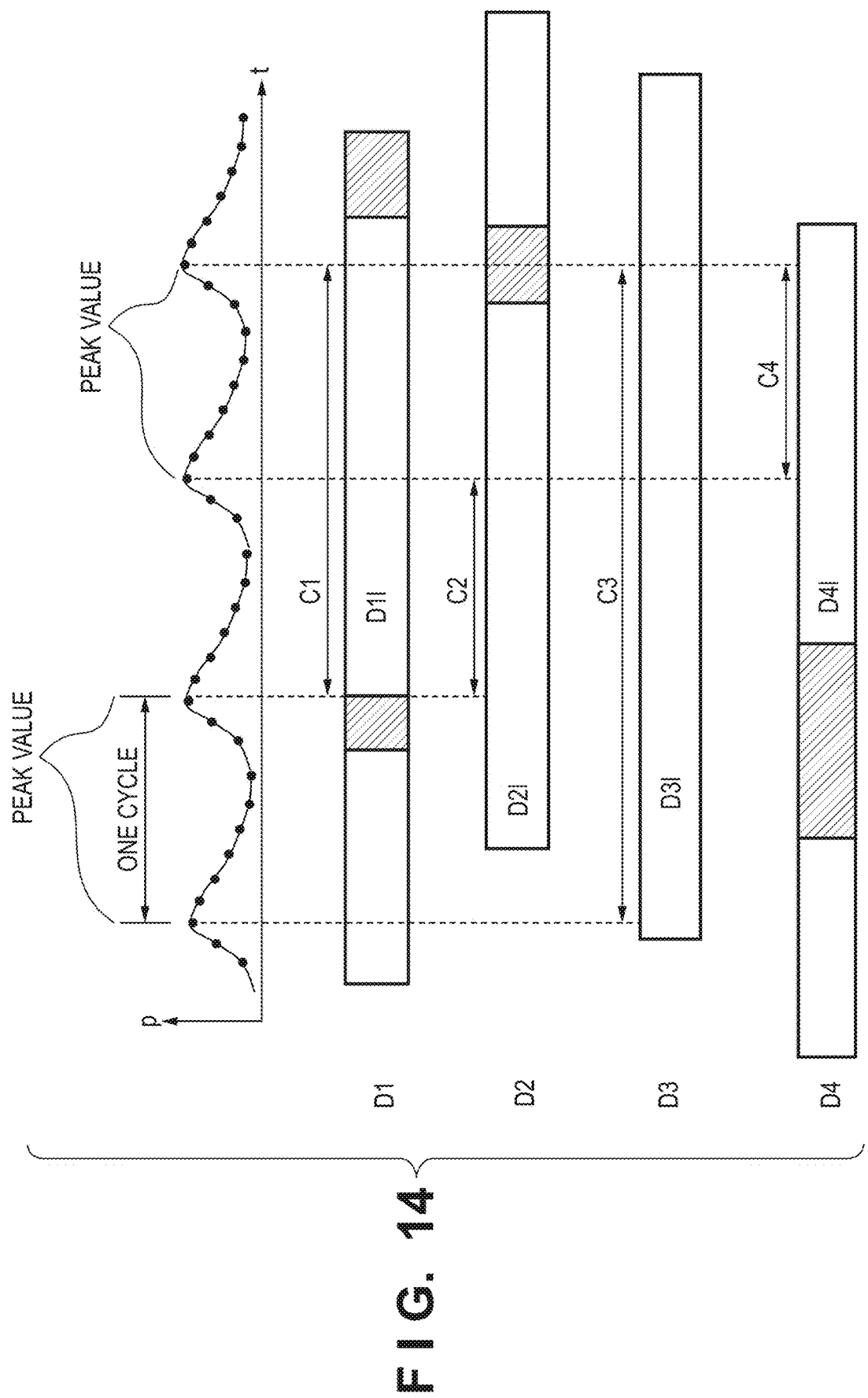
FIG. 14 is a view for explaining processing executed in step S1340 according to the third embodiment.

The image forming processing executed in step S930 will be described in detail with reference to a flowchart shown in FIG. 13 and FIG. 14.

<Step S1310> The image forming method change unit 132 receives an exceptional frame list from the exceptional frame determination unit 131. If one or more exceptional frames exist, the process advances to step S1320. On the other hand, if there is no exceptional frame, the process advances to step S1330.

<Step S1320> An image selection unit 1321 selects a sub moving image Dnl from an SLO moving image Dn including exceptional frames. Referring to FIG. 14, white portions indicate normal frames of the SLO moving images D1 to D4 obtained by repeatedly performing an imaging operation, and gray (hatched) portions indicate exceptional frames. In the uppermost part of FIG. 14, the pulse data obtained in the imaging operation is shown. Since obtainment of the pulse data starts at the start of an operation of capturing each SLO moving image Dn, the phases of the pulse data corresponding to the initial frames of the respective SLO moving images are different from each other. The image selection unit 1321 selects, as a sub moving image Dnl, a longest frame sequence without any exceptional frames from each SLO moving image Dn. In FIG. 14, sub moving images D11, D21, D31, and D41 are selected.

<Step S1330> The luminance correction unit 136 adjusts the luminance between the sub moving images Dnl. In this embodiment, the unit 136 obtains the histogram of each sub moving image Dnl, and performs linear transformation for the luminance values of sub moving images other than a sub moving image Dnl with luminance characteristics which are closest to a luminance average value Ga and luminance variance value Ja obtained by capturing a schematic eye so that they coincide with a luminance average Gn and luminance variance Jn of the sub moving image Dnl.

Note that the luminance adjustment method is not limited to this, and an arbitrary luminance adjustment method may be used. For example, the luminance value of each sub moving image may undergo linear transformation to match its luminance average value and luminance variance value with the luminance average value Ga and luminance variance value Ja obtained by capturing a schematic eye.

Alternatively, a blood vessel area Vn may be extracted from each SLO moving image Dn using a known blood vessel extraction method, and a histogram Kvn limited to the blood vessel area Vn may be generated, and then the luminance values may be adjusted so that luminance statistics (average and variance) calculated based on the histogram Kvn coincide with specific values (Gv and Jv) which facilitate recognition of the blood vessel area Vn.

<Step S1340> Based on the pulse data Pn obtained together with the longest sub moving image Dnl, the connection unit 138 extracts the sub moving images Snl and connects them. In this embodiment, the peak interval of a pulse wave signal value is set as one cycle, and longest sub moving images Snl (to be referred to as sub moving images Cn hereinafter) in cycles extracted from the sub moving images Dnl are connected based on the imaging times in chronological order. That is, sub moving images C1 to C4 extracted from the sub moving images D1 to D4 are connected in the order of C1+C2+C3+C4, thereby forming a new SLO moving image D. Note that although the peak positions of the pulse data are used in this embodiment, the moving images may be connected using an arbitrary phase of the pulse data.

If the number of frames of the new SLO moving image D obtained by connecting the sub moving images is equal to or larger than Tn, Tn frames are extracted from the beginning of the connected SLO moving image D, and an image header (attribute information) is added to form an SLO moving image Df for observation/measurement. On the other hand, if the number of frames of the new SLO moving image D obtained by connecting the sub moving images is smaller than Tn, a warning to perform an imaging operation again is displayed.

Note that the method of extracting the sub moving images Cn is not limited to this, and an arbitrary method may be used. For example, the sub moving image D11 is used as the sub moving image C1 intact, and the sub moving image C2 is extracted for the sub moving image D21 by setting, as the start frame of the sub moving image C2, a frame having a phase of the pulse data corresponding to the last frame of the sub moving image C1. That is, the start frame of a sub moving image Cn is set according to the phase of pulse data included in the last frame of a sub moving image Cn−1, and the last frame of the sub moving image Cn is set according to the phase of pulse data included in the last frame of a sub moving image Dnl, thereby performing extraction processing. Although the SLO moving images D1 to D4 are separate moving images in FIG. 14, a frame sequence may be extracted and connected for one SLO moving image as described above, thereby obtaining a moving image with a necessary length.

As described above, according to the third embodiment, the image forming apparatus 10 extracts a sub moving image Dnl including a longest frame sequence without any exceptional frames from each of the SLO moving images Dn obtained by repeatedly performing an imaging operation. The luminance correction unit 136 adjusts the luminance between the sub moving images Dnl. The connection unit 138 extracts partial images Cn from sub moving images Dnl having undergone the above luminance adjustment operation to perform a connection operation based on the phase of pulse data. The connection unit 138 then connects the extracted partial images Cn to form an SLO moving image Df including an area and the number of frames necessary for observation/measurement. With this arrangement, it is possible to automatically form an SLO moving image Df which includes a necessary area (spatial size) and can be observed/measured for a longer time.

Fourth Embodiment

In the fourth embodiment, exceptional frame determination is performed while obtaining SLO images by an SLO apparatus 20. The SLO apparatus 20 is instructed to continue an imaging operation until a continuous frame sequence Sl without any exceptional frames includes a predetermined number Tn of frames, thereby forming an SLO moving image Df which includes the number Tn of frames necessary for observation/measurement. With this arrangement, it is possible to automatically form, at high speed, an SLO moving image Df which does not include any exceptional frame or any frame having undergone image interpolation but includes an area (spatial size) and the number of frames (time) necessary for observation/measurement.

Figure 15:
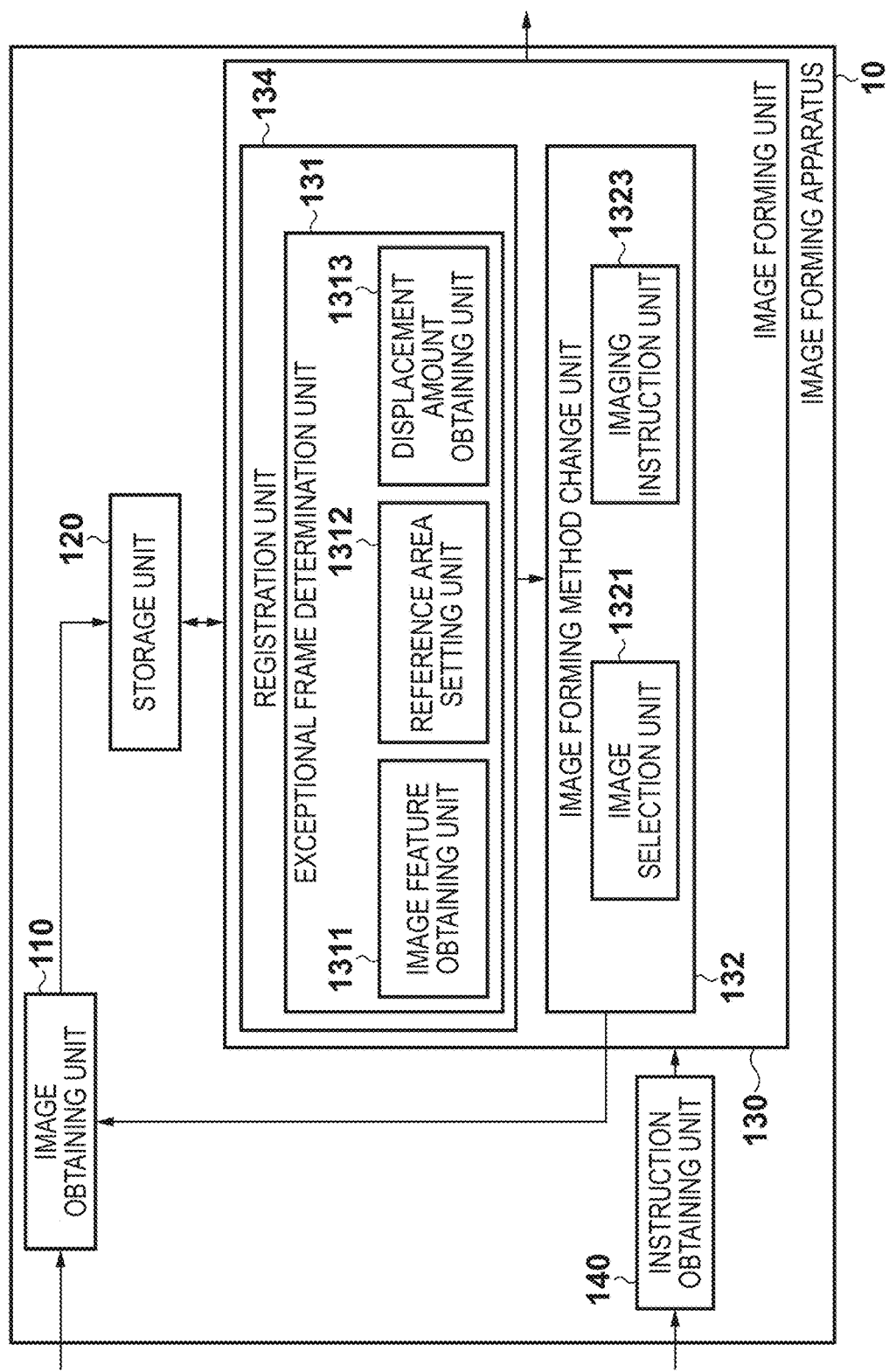
FIG. 15 is a block diagram showing an example of the functional arrangement of an image forming apparatus according to the fourth embodiment.
Figure 16:
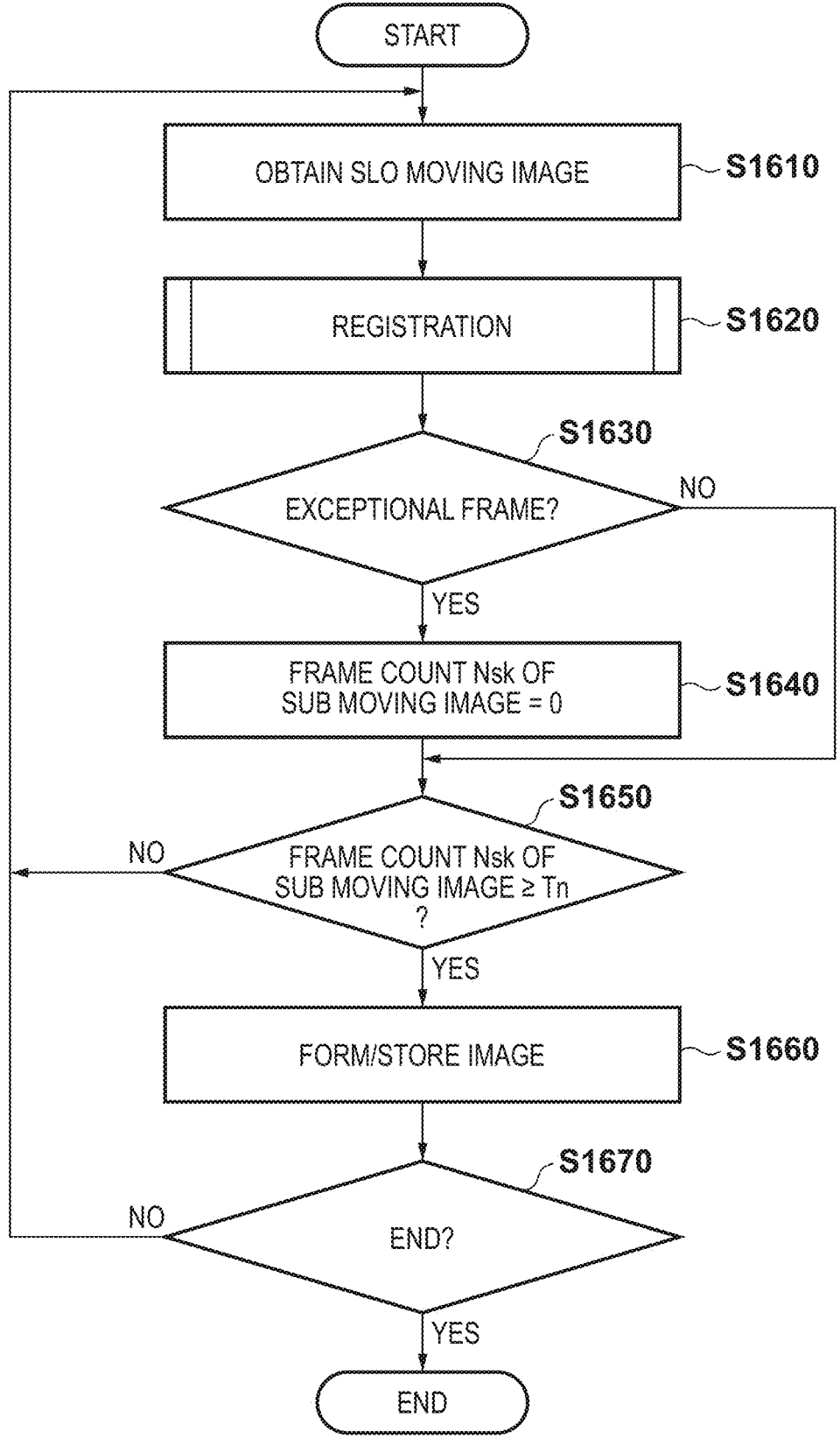
FIG. 16 is a flowchart illustrating processing executed by the image forming apparatus according to the fourth embodiment.

FIG. 15 is a functional block diagram showing an image forming apparatus 10 according to the fourth embodiment. The image forming apparatus 10 in the fourth embodiment is different from that in the second embodiment (FIG. 8) in that an image forming method change unit 132 includes an imaging instruction unit 1323 instead of the exceptional frame replacement method instruction unit 1322. The procedure of image forming processing according to the fourth embodiment is as shown in FIG. 16. Processing in step S1670 is the same as that in the second embodiment (step S960 of FIG. 9). Each process in the fourth embodiment will be described below.

<Step S1610> An image obtaining unit 110 requests the SLO apparatus 20 to obtain an SLO moving image D and a fixation target position F. In response to a request from the image obtaining unit 110, the SLO apparatus 20 captures frames Di of the SLO moving image D.

More specifically, in response to the obtaining request from the image obtaining unit 110, the SLO apparatus 20 obtains the frames Di of the SLO moving image D and the fixation target position F, and transmits them. Note that the fixation target position F may be obtained and transmitted only when obtaining a first frame D1. The image obtaining unit 110 receives the frame D1 and fixation target position F from the SLO apparatus 20 via a LAN 30. The image obtaining unit 110 stores the received frame Di and fixation target position F in a storage unit 120. Furthermore, an image forming unit 130 adds 1 to the value of a frame count Nsk of a continuous non-exceptional frame sequence. Note that the frame count Nsk has been initialized to 0 before the start of the processing of FIG. 16.

<Step S1620> A registration unit 134 performs registration and exceptional frame determination for one frame of the SLO moving image D received in step S1610. Note that the processing in step S1620 will be described later with reference to a flowchart shown in FIG. 17.

<Step S1630> The image forming method change unit 132 receives, from an exceptional frame determination unit 131, a determination result indicating whether the frame received in step S1610 is an exceptional frame. If the frame of the SLO moving image received in step S1610 is an exceptional frame, the process advances to step S1640; otherwise, the process advances to step S1650.

<Step S1640> If it is determined in step S1630 that the frame is an exceptional frame, the image forming method change unit 132 sets 0 in the frame count Nsk of the continuous non-exceptional frame sequence (sub moving image), and advances the process to step S1650. If it is not determined that the frame Di is an exceptional frame, the process directly advances to step S1650.

<Step S1650> The image forming method change unit 132 refers to the frame count Nsk of the non-exceptional frame sequence. If Nsk≥Tn, the imaging instruction unit 1323 instructs, via the image obtaining unit 110, the SLO apparatus 20 to terminate the imaging operation, and advances the process to step S1660. On the other hand, if the frame count Nsk of the non-exceptional frame sequence is smaller than Tn, the imaging instruction unit 1323 instructs, via the image obtaining unit 110, the SLO apparatus 20 to continue the imaging operation or perform an imaging operation again.

<Step S1660> The image forming unit 130 adds a header portion to the obtained non-exceptional frame sequence, and forms an SLO moving image Df for observation/measurement. The formed SLO moving image Df is stored in a data server 40.

<Step S1670> Processing in step S1670 is the same as that in step S460 (FIG. 4) or S960 (FIG. 9).

The registration processing executed in step S1620 will be described in detail with reference to the flowchart shown in FIG. 17.

<Step S1710> The exceptional frame determination unit 131 performs exception determination using one frame Di of the obtained SLO moving image D. The practical exception determination method is the same as that in the second embodiment (step S1010 of FIG. 10). If the frame Di of the obtained SLO moving image D is an exceptional frame, a reference frame number is not set.

<Step S1720> A reference area setting unit 1312 refers to the reference frame number. If the reference frame number has been set, the process advances to step S1740; otherwise, the process advances to step S1730.

<Step S1730> If the frame Di of the obtained SLO moving image D is not an exceptional frame, the frame Di is set as a reference frame, thereby terminating the registration processing. On the other hand, if the frame Di is an exceptional frame, the registration processing ends without executing any processing.

<Step S1740> The registration unit 134 performs registration between the reference frame and the frame Di (non-exceptional frame) of the SLO moving image D. As a practical registration method, it is only necessary to execute registration processing for one frame using the registration method described in steps S1030 and S1040 of the second embodiment. Note that the registration method is not limited to this. For example, fine registration processing may be omitted to improve the speed of the registration processing.

<Step S1750> Exceptional frame determination is performed for the frame Di which has undergone registration in step S1740. As a practical exceptional frame determination method, it is only necessary to execute, for one frame, the exceptional frame determination processing described in step S1050 of the second embodiment.

As described above, according to the fourth embodiment, the image forming apparatus 10 performs, for each frame, an operation of obtaining the frame Di by the SLO apparatus 20 and performing exceptional frame determination. If the number of frames of a non-exceptional frame sequence is smaller than a predetermined number Tn of frames, the image forming apparatus 10 instructs the SLO apparatus 20 to continue the imaging operation, thereby capturing a next frame. When the number of frames of the non-exceptional frame sequence reaches the predetermined number Tn of frames necessary for observation/measurement, the image forming apparatus 10 forms an SLO moving image Df. With this arrangement, it is possible to automatically form, at high speed, an SLO moving image Df which does not include any exceptional frame or any frame having undergone image interpolation, but includes an area (spatial size) and the number of frames (time) necessary for observation/measurement.

As described above, according to each of the above-described embodiments, it is possible to automatically form an SLO moving image which includes no exceptional frame inappropriate for observing/measuring a tissue/cell/lesion, but includes an area and the number of frames necessary for observation/measurement.

Other Embodiments

Although a frame sequence including continuous frames without any exceptional frames is generated in the above-described embodiments, it is possible to change a frame rate as needed based on setting information to meet a frame rate required by a doctor, a case, or a part to be diagnosed. For example, the image forming unit 130 can decrease the frame rate by thinning out some frames according to the setting information. The image forming unit 130 can also increase the frame rate by inserting frames according to the settings.

Figure 5A:
FIGS. 5A to 5E are views for explaining problems associated with general SLO image forming processing.
Figure 5B:
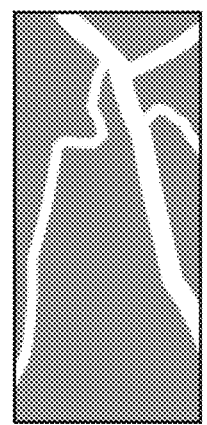
Figure 5C:
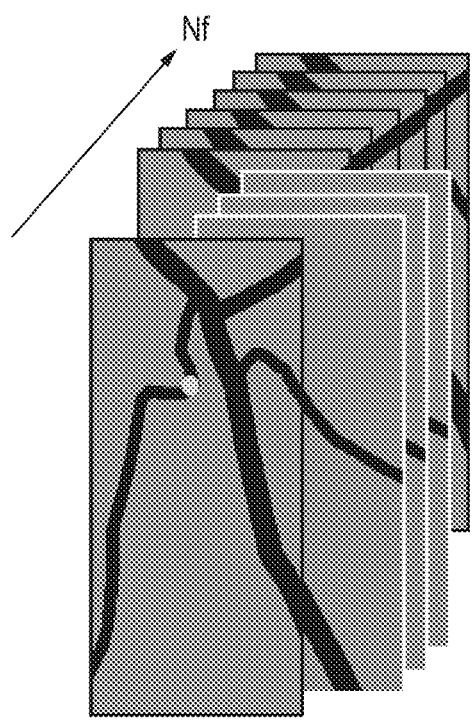
Figure 5D:
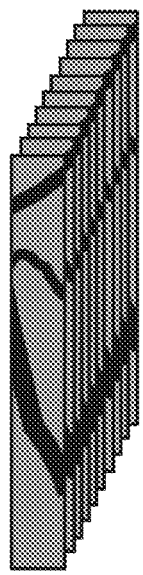
Figure 5E:
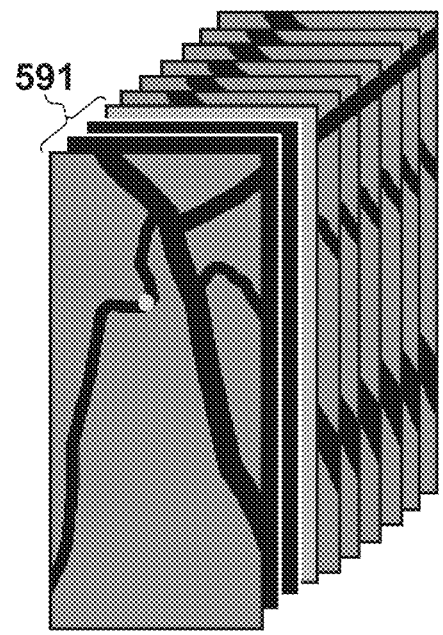

A frame sequence without any exceptional frames is generated in the above-described embodiments. If an area where observation/measurement processing is possible becomes small for all frames (FIG. 5D) due to fixation disparity as shown in FIG. 5C, it is possible to generate a moving image including the frames for which the area has become small. For an exceptional frame group, obtained in the above-described embodiment, between a first frame sequence and a second frame sequence, the image forming unit 130 determines whether a factor for an exceptional frame is that a measurement-enable area has become small due to fixation disparity or the like. If the factor is that the area has become small, the image forming unit 130 inserts a third frame sequence, for which the area has become small, between the first frame sequence and the second frame sequence. The unit 130 then connects the first to third frame sequences to generate a moving image. The image forming apparatus 10 displays the generated moving image on a monitor 305. The above processing enables to present an area necessary for observation/measurement to the user while ensuring the temporal continuity of the moving image.

Although the embodiments have been described in detail, the present invention can adopt an embodiment in the form of, for example, a system, apparatus, method, program, or storage medium. More specifically, the present invention may be applied to a system constituted by a plurality of devices, or an apparatus comprising a single device.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-034538, filed Feb. 20, 2012, which is hereby incorporated by reference herein in its entirety.

The invention claimed is:

1. An image forming apparatus comprising:
a processor and a memory configured to together function as units comprising
(1) a determination unit configured to determine whether each frame of a plurality of frames constituting a frame sequence of a moving image of an eye of an examinee is an exceptional frame based on an image feature of each frame of the plurality of frames, wherein each frame of the moving image is associated with a phase of a pulse wave from a biological signal of the examinee obtained in capturing the moving image;
(2) an extracting unit configured to extract a first sub moving image and a second sub moving image from a plurality of sub frame sequences which are included in the moving image and which include continuous frames without any exceptional frame determined by the determination unit, wherein the second sub moving image is extracted such that a phase of the pulse wave of a start frame of the second sub moving image and a phase of the pulse wave of a last frame of the first sub moving image coincide; and
(3) a generation unit configured to generate a new moving image by connecting the start frame of the second sub moving image to the last frame of the first sub moving image.

2. The apparatus according to claim 1, wherein the image feature includes at least one of a luminance, an amount of distortion, and a signal to noise ratio.

3. The apparatus according to claim 1, wherein the determination unit determines an exceptional frame based on a displacement amount with respect to a reference area set for one of the plurality of frames.

4. The apparatus according to claim 3, wherein the reference area is the whole of the one frame or a portion specified by image processing of the one frame or a user.

5. The apparatus according to claim 1, wherein the processor and the memory are configured to further function as a registration unit configured to perform inter-frame registration for the plurality of frames,
wherein the determination unit determines an exceptional frame based on an image feature obtained in the inter-frame registration or an image feature obtained from a frame having undergone the registration.

6. The apparatus according to claim 5, wherein the determination unit determines an exceptional frame based on an image feature of a single frame before the inter-frame registration, and determines an exceptional frame based on a difference in image feature between frames after the inter-frame registration.

7. The apparatus according to claim 1, wherein the extracting unit extracts the first sub moving image and the second sub moving image from the plurality of sub frame sequences in length order.

8. The apparatus according to claim 7, wherein if a longest sub frame sequence does not include a predetermined number of frames, the generation unit generates an interpolation frame using preceding and succeeding non-exceptional frames of a frame which has been determined as an exceptional frame, and uses the interpolation frame as a non-exceptional frame to generate a continuous frame sequence including the predetermined number of frames.

9. The apparatus according to claim 1, wherein if a plurality of sub moving images each including frames, the number of which exceeds the predetermined number, are obtained, the generation unit generates the new moving image using a sub moving image for which a statistic of a displacement amount between the frames of the sub moving image is smallest.

10. The apparatus according to claim 1, wherein the processor and the memory are configured to further function as an instruction unit configured to instruct to, if a number of frames of the sub moving image extracted by the extracting unit is smaller than a predetermined number, perform an imaging operation again or continue an imaging operation.

11. The apparatus according to claim 1, wherein the moving image and the new moving image have the same frame rate.

12. The apparatus according to claim 1, wherein the number of frames constituting the frame sequence of the moving image is larger than that of the new moving image.

13. The apparatus according to claim 1, wherein the exceptional frame is at least one of (a) a frame where a luminance is low due to blinking, (b) a frame where image distortion has occurred due to involuntary eye movement, or (c) a frame where a signal-to-noise ratio is low due to an aberration correction failure.

14. The apparatus according to claim 1, wherein the pulse wave based on a biological signal is obtained using a sphygmograph.

15. The apparatus according to claim 1, wherein the first sub moving image and the second sub moving image are extracted at predetermined positions in the peak interval of the pulse wave.

16. The apparatus according to claim 15, wherein the predetermined position is a peak position of the pulse wave.

17. An apparatus-implemented image forming method for an image forming apparatus, the image forming method comprising the steps of:
determining whether each frame of a plurality of frames constituting a frame sequence of a moving image of an eye of an examinee is an exceptional frame based on an image feature of each frame of the plurality of frames, wherein each frame of the moving image is associated with a phase of a pulse wave from a biological signal of the examinee obtained in capturing the moving image;
extracting a first sub moving image and a second sub moving image from a plurality of frame sequences which are included in the moving image and which include continuous frames without any exceptional frame determined in the determining step, wherein the second sub moving image is extracted such that a phase of the pulse wave of a start frame of the second sub moving image and a phase of the pulse wave of a last frame of the first sub moving image coincide; and
automatically generating a new moving image by connecting the start frame of the second sub moving image to the last frame of the first sub moving image.

18. A non-transitory computer-readable storage medium storing a program for causing a computer comprising a processor and a memory to execute an image forming method for an image forming apparatus, the image forming method comprising the steps of:
determining whether each frame of a plurality of frames constituting a frame sequence of a moving image of an eye of an examinee is an exceptional frame based on an image feature of each frame of the plurality of frames, wherein each frame of the moving image is associated with a phase of a pulse wave from a biological signal of the examinee obtained in capturing the moving image;

extracting a first sub moving image and a second sub moving image from a plurality of sub frame sequences which are included in the moving image and which include continuous frames without any exceptional frame determined in the determining step, wherein the second sub moving image is extracted such that a phase of the pulse wave of a start frame of the second sub moving image and a phase of the pulse wave of a last frame of the first sub moving image coincide; and automatically generating a new moving image by connecting the start frame of the second sub moving image to the last frame of the first sub moving image.

* * * * *